United States Patent [19]

Bormann et al.

[11] 4,093,735
[45] June 6, 1978

[54] 5-SULFAMOYLBENZOIC ACID DERIVATIVES CARRYING A HETEROCYCLIC SUBSTITUENT

[75] Inventors: Dieter Bormann, Kelkhein, Taunus; Wulf Merkel, Neuenhain, Taunus; Roman Muschaweck, Frankfurt am Main, all of Germany

[73] Assignee: Hoechst Aktiengesellschaft, Frankfurt am Main, Germany

[21] Appl. No.: 740,741

[22] Filed: Nov. 10, 1976

Related U.S. Application Data

[62] Division of Ser. No. 570,649, Apr. 23, 1975, Pat. No. 4,010,273.

[30] Foreign Application Priority Data

Apr. 25, 1974  Germany ............................ 2419970

[51] Int. Cl.$^2$ .......................................... C07D 207/20
[52] U.S. Cl. ................................ 424/274; 260/326.41
[58] Field of Search .................... 260/326.41; 424/274

[56] References Cited

U.S. PATENT DOCUMENTS

| 3,565,920 | 2/1971 | Werner | 260/347.2 |
| 3,939,267 | 2/1976 | Werner | 424/319 |

OTHER PUBLICATIONS

Peter W. Feit, Journal of Medicinal Chemistry, (1971), vol. 14, No. 5, pp. 432–435.

*Primary Examiner*—Norma S. Milestone
*Attorney, Agent, or Firm*—Curtis, Morris & Safford

[57] ABSTRACT

5-Sulfamoylbenzoic acids substituted in 4-position by various substituents and in 3-position by a cyclic amino group having sali-diuretic properties.

4 Claims, No Drawings

5-SULFAMOYLBENZOIC ACID DERIVATIVES CARRYING A HETEROCYCLIC SUBSTITUENT

This application is a division of application Ser. No. 570,649 filed Apr. 23, 1975, now U.S. Pat. No. 4,010,273.

The invention relates to 5-sulfamoylbenzoic acid derivatives carrying heterocyclic substituents and corresponding to the general formula I

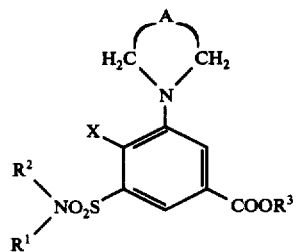

in which $R^1$ and $R^2$, which may be identical or different, represent hydrogen or alkyl of 1 to 4 carbon atoms, and, if $R^1$ represents hydrogen, $R^2$ may also be alkoxymethyl of 2 to 5 carbon atoms in the alkyl radical, phenoxymethyl or phenylthiomethyl; $R^3$ represents hydrogen, alkyl of 1 to 4 carbon atoms, cycloalkyl of 5 or 6 carbon atoms, one of which may be replaced by oxygen or sulfur, phenyl or benzyl which may be substituted in the phenyl nucleus by nitro groups, alkyl groups of 1 to 3 carbon atoms, alkoxy groups of 1 to 3 carbon atoms or halogen, or $R^3$ reperesents benzhydryl or alkanoyloxymethyl of 3 to 5 carbon atoms, X represents halogen, $CF_3$, $CCl_3$, straight-chain or branched, saturated or unsaturated alkyl or alkoxy of up to 6 carbon atoms, benzyl which may be substituted by halogen, hydroxy, amino, lower alkyl or lower alkoxy, or X represents one of the groups $O-R^4$, $S-R^4$, $SO-R^4$, $SO_2-R^4$ and $NR^4R^5$, in which $R^4$ represents phenyl which may be substituted by Hal, OH, $NH_2$, $CF_3$, $NO_2$ alkyl or alchain or branched alkyl of 1 to 4 carbon atoms which may be substituted by phenyl, pyridyl, furyl or thienyl and $R^5$ represents hydrogen, straight chain or branched alkyl of 1 to 4 carbon atoms, and the group $NR^4R^5$ may also represent a saturated, heterocyclic, 5- to 6-membered ring which may be interrupted by O-, N- or S-atoms, A represents a single bond or an alkylene of up to 3 carbon atoms which may be unsaturated, interrupted by O-, N- or S-atoms or substituted by halogen atoms and/or by alkyl, aralkyl, aryl groups that may be branched, or by mono-nuclear hetero-aromatic rings, or A may represent an ortho-phenylene radical or the grouping

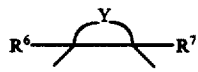

in which Y represents a single bond or an alkylene group of 1 to 4 carbon atoms, and $R^6$ and $R^7$, which may be identical or different, represent hydrogen, halogen or alkyl of 1 to 4 carbon atoms, and their physiologically tolerated salts with bases or acids.

Preferred compounds of the formula I of the invention are those in which the radicals $R^1$ and $R^2$ represent hydrogen, or, if $R^1$ = H, $R^2$ represents alkyl of 1 to 4 carbon atoms, $R^3$ represents hydrogen, alkyl of 1 to 4 carbon atoms or benzyl; X represents benzyl, $-OR^4$, $-SR^4$, $-SO-R^4$, $R^4$ being phenyl radical which may be substituted in any position, once or several times, by, for example Cl, OH, $CF_3$, straight-chain or branched alkyl of 1 to 3 carbon atoms, alkylamino, dialkylamino or alkoxy of 1 to 2 carbon atoms or $NH_2$; and A represents a single bond or an alkylene of up to 2 carbon atoms which may be unsaturated or substituted once or several times by halogen atoms, phenyl or lower alkyl. Compounds in which X is phenoxy, phenylthio, phenylsulfinyl and benzyl are of particular importance.

The invention furthermore relates to a process for preparing the compounds of the general formula I

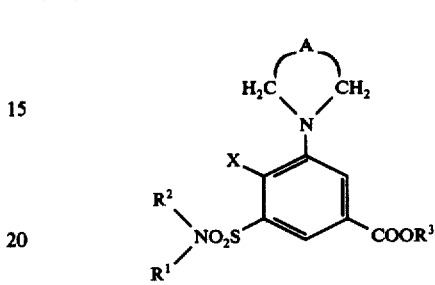

in which the radicals $R^1$ to $R^3$, A and X have the meanings given above, which comprises (a) reducing a 3-substituted sulfamoylbenzoic acid derivative of the general formula II

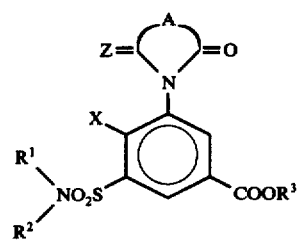

in which the radicals $R^1$ to $R^3$, A and X have the meanings given above, and in which the hydroxy, amino or mercapto groups may be blocked by customary protective groups, and Z represents two hydrogen atoms or one oxygen atom, by reacting with a boron hydride or complex boron hydride in the presence of a Lewis-acid, or (b) reacting a 5-halogeno-sulfonylbenzoic acid derivative of the general formula III

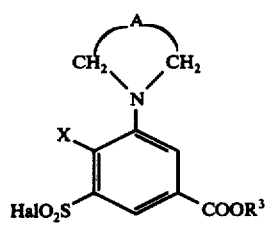

in which $R^3$, A and X have the meanings given above, and Hal represents a halogen atom, with an amine of the formula

in which $R^1$ and $R^2$ have the meanings given above, or (c) converting by hydrolysis or mild oxidation reactions sulfamoyl compounds of the general formula IV

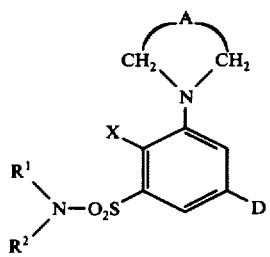

in which the radicals R¹ and R², A and X have the meanings given above and D represents a radical which may be transformed into a carboxylic acid, into the 5-sulfamoylbenzoic acids of the formula I (R³ = H), or (d) treating sulfamoylbenzoic acid derivatives of the general formula V

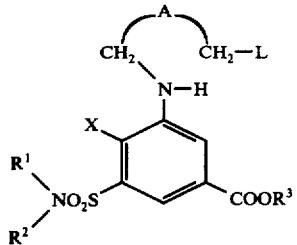

in which the radicals R¹ to R³, A and X have the meanings given above and L represents a "leaving group", with acids or bases in order to eliminate HL, or (e) cyclisizing sulfamoylbenzoic acid derivatives of the general formula VI

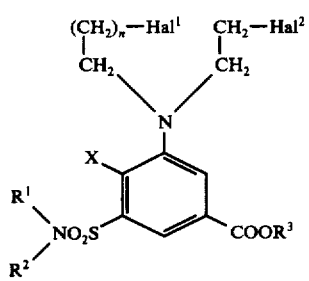

in which the radicals R¹ to R³ and X have the meanings given above, Hal¹ and Hal², which may be identical or different, represent halogen, preferably chlorine and/or bromine, and n represents the number 0 to 2, by the reaction with metals in accordance with the conditions of the Wurtz-Fittig synthesis or by the reaction with primary amines, NH₃ or H₂S to form compounds of the general formula I, or (f) reducing corresponding 3-N-pyrrolo-compounds of the general formula VII

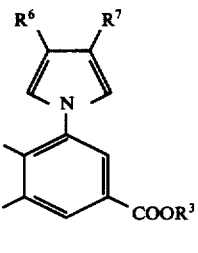

or (g) nitrating sulfamoylbenzoic acid derivatives of the general formula VIII

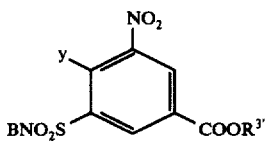

in which Y represents a halogen atom, R³' represents hydrogen, alkyl of 1 to 4 carbon atoms or cycloalkyl of 5 or 6 ring members and B represents a protective group of the general formula

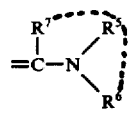

in which R⁴, R⁵ and R⁶ represent identical or different lower alkyl groups and in which R⁴ may also represent hydrogen, and/or two substituents each R⁴, R⁵ or R⁶ may be bound in a cycle with each other, and esterifying the compounds of the formula IX obtained

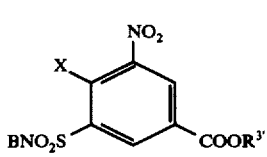

if R³' is hydrogen, and reacting the compounds of the formula IX obtained, in which B and Y have the meanings given above while R³' means alkyl or cycloalkyl with compounds of the formula XH, in which X has the meaning given above, and reducing the compounds of the formula X so obtained

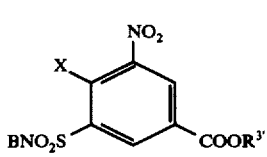

in which B and Y have the meanings given above and R³' represents an alkyl radical of 1 to 4 carbon atoms or cycloalkyl or 5 or 6 members, and reacting the compounds obtained of the general formula XI

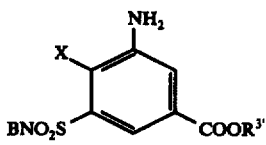

in which B, X and $R^{3'}$ have the meanings given above, with compounds of the general formula XII

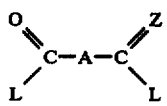

in which A and Z have the meanings given above, and L represents a "leaving group" or both L's together represent an oxygen atom, and reducing the compounds of the general formula XIII so obtained

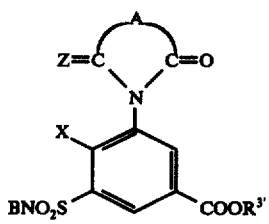

in which the radicals A, B and $R^{3'}$, X and Z have the meanings given above, in the presence of Lewis acids with boron hydride or with complex boron hydrides, and hydrolyzing the compounds of the general formula XIV so obtained

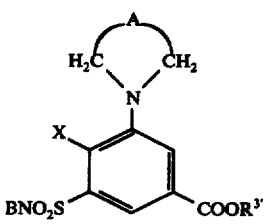

in which A, B, X and $R^{3'}$ have the meanings given above, and, if desired, in compounds of the formula I obtained according to (a) to (g), hydrogenating double bonds or introducing double bonds by elimination reactions and/or esterifying free carboxylic acids of the formula I ($R^3$ = H) and/or converting carboxylic acid esters of the general formula I ($R^3$ = $R^{3'}$) by hydrolysis or elimination reactions into the carboxylic acids ($R^3$ = H) and/or setting free hydroxy, amino or mercapto groups by separation of a protective group and/or transforming carboxylic acids of the formula I ($R^3$ = H) by treatment with bases or acids into their physiologically tolerated salts.

In process (a) according to the invention, it is surprising that it is possible to reduce sulfamoylbenzoic acid derivatives of the formula II by means of boron hydrides or complex borohydrides in the presence of Lewis acids without affecting the other groups in the molecule. The end products are obtained in excellent yields in this procedure.

The sulfamoylbenzoic acid derivatives of the formula II which are used in accordance with the invention are accessible by various processes. For example, the 3-imido-5- sulfamoylbenzoic acid derivatives of the formula II (Z = O) are obtained from the 3-amino-5-sulfamoylbenzoic acid derivatives, which are known from the literature, of the formula XV in which the radicals $R^1$ to $R^3$ and X have the meanings indicated, by reacting these amino compounds with dicarboxylic acid derivatives of the general formula XVI which are capable of forming imides and in which A has the meaning indicated, Z represents O and L denotes a "leaving group," preferably a halogen atom, a trialkylammonium group or the radical OR' of an activated ester. For this acylation reaction, hydroxyl, amino and/or mercapto groups in other positions of the molecule should be blocked by means of customary protective groups.

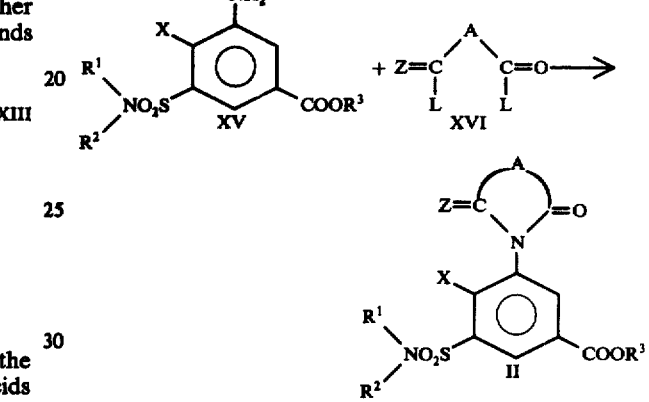

Examples of dicarboxylic acids which can be converted into their dicarboxylic acid halides are succinic acid, methylsuccinic acid, 2,3-dimethylsuccinic acid, glutaric acid, 2-methylglutaric acid, phthalic acid, cis-cyclopropanedicarboxylic acid, cyclobutane-1,2-cis-dicarboxylic acid, cyclohexane-1,2-cis-dicarboxylic acid, bromosuccinic acid or diglycolic acid. The reaction of these dicarboxylic acid derivatives with the amino compounds of the formula XV is carried out under the conditions of the known Schotten-Baumann reaction.

It is also possible to use the anhydrides of these dicarboxylic acids. The carboxylic acid derivatives of the formula XVII which are formed primarily in many cases, change into the imido compounds (II) directly, with elimination of water.

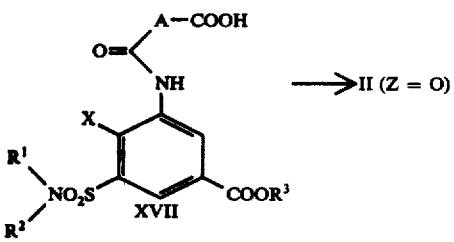

The reaction can be followed by thin layer chromatography. Depending on the reaction conditions chosen, particularly if the reaction mixture is heated to temperatures of 150° to 250° C, the cyclised products are obtained in high yields.

The anhydride is advantageously used in a substantial excess, say in a 2- or 3-fold excess, and the reaction is carried out in the absence of a solvent. If unsaturated dicarboxylic acid anhydrides are used, such as, for example, maleic anhydride, a viscous oil is formed on fusion in the reaction with amino compounds of the formula XV at temperatures of 150° to 200° C, and this oil changes after some time, with elimination of water, into the unsaturated imido compounds of the formula XVIII

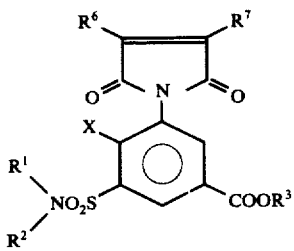

in which the radicals $R^1$ to $R^3$, $R^6$, $R^7$ and X have the meanings indicated. The double bond of this imido compound makes possible a large number of reactions, for example it can be hydrogenated, whereupon imido compounds of the formula II are formed in which Z represents O and A represents an ethylene group.

The starting compounds of the formula II in which Z represents two hydrogen atoms, are accessible by various processes, for example from the amino compounds of the formula XV by reaction with ω-substituted carboxylic acid derivatives of the formula XVI in which Z represents two hydrogen atoms, according to the conditions of the Schotten-Baumann reaction and subsequent cyclisation of the resulting amido compounds of the formula XIX

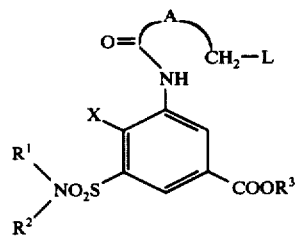

with elimination of H—L.

The following examples of such carboxylic acid derivatives of the formula XVI may be mentioned: ω-chloropropionic acid chloride, ω-chloropropionic acid bromide, ω-chlorobutyric acid chloride, ω-bromobutyric acid chloride, ω-bromobutyric acid phenyl ester and the chloride of trimethylammoniumbutyric acid chloride.

The bases required for the elimination of the grouping H—L are preferably tertiary organic bases, such as pyridine, triethylamine or N,N-dimethylaniline, which are used in the stoichiometric quantity or in a substantial excess, for example they are used as the solvent at the same time.

The amido or imido derivatives may be used in the reduction according to the invention as free acids or in the form of their salts which do not interfere with the reduction, such as, for example, the alkali metal salts or alkaline earth metal salts.

In order to obtain particularly pure reaction products in high yield, it is advantageous to use 5-sulfamoylbenzoic acid esters for the reduction.

The esters can be prepared from the acids by processes which are known from literature. Suitable esters are especially the lower alkyl esters of 1 to 5 carbon atoms, such as the methyl, ethyl, propyl, butyl or n-pentyl ester, the benzyl ester or p-methoxybenzyl ester and the t-butyl ester, the benzhydryl ester and acyloxymethyl ester wherein the acyl radical represents the radical of a lower aliphatic carboxylic acid, for example the acetyl or tert.-butyryl radical.

Suitable reducing agents are complex borohydrides or diborane in the presence of Lewis acids. In the reduction of lactams of the formula II (Z = 2 H), it is possible to operate with diborane in the presence of Lewis acids. Imides (Z = O), on the other hand, require the use of complex borohydrides in the presence of Lewis acids in order to obtain good yields. The reducing agents may be introduced into the reaction mixture by taking suitable protective measures, for example the use of nitrogen as an inert gas. In the case of using diborane, it is simpler for carrying out the reaction to take it up in a solvent and to use the solution for the reduction. Suitable solvents are especially ethers, for example tetrahydrofurane or diethylene glycol dimethyl ether.

The complex hydrides of boron used in this method of reduction are, for example, the alkali metal boranates such as lithium borohydride, sodium borohydride or potassium borohydride, or the alkaline earth metal boranates such as calcium borohydride, but also zinc borohydride or aluminium borohydride. If Lewis acids are added, these borohydrides reduce the amide or imide groups present in the compounds and do so, surprisingly, without appreciably attaching the carboxylic acid ester function.

Suitable Lewis-acids within the meaning of the invention are especially aluminium chloride, titanium tetrachloride, tin tetrachloride, ferric chloride, and boron trifluoride and its addition products, for example, boron trifluoride etherate. In this case there is the possibility that diborane may be formed in situ in the reaction of the boron trifluoride etherate, for example with sodium borohydride (c.f. Fieser, Fieser: Reagents for Organic Synthesis, John Wiley and Sons, Inc., New York, Vol. 1, page 199).

In order to obtain a particularly high yield and particularly pure end products, it is advantageous first to introduce the Lewis acid together with the compounds of the formula II and then to add the complex borohydride.

It is particularly advantageous to use the Lewis acid in excess and the complex borohydride in at least a stoichiometric quantity, relative to the amide group to be reduced.

Thus, advantageous results are obtained by adding, for example in the case of titanium tetrachloride, three times the stoichiometrical quantity of $NaBH_4$, and when using boron trifluoride etherate, by using the complex borohydride in the stoichiometric quantity, relative to the particular number of amide group to be reduced.

In carrying out the reduction it is unimportant whether the substances to be reduced are introduced as imido compounds of the formula II (Z = O) or as amido compounds (Z = 2H). Surprisingly, in a one-vessel reaction, the imido compounds change directly into the sulfamoylbenzoic acid derivatives of the formula I. The reduction is carried out in a solvent. Examples of suitable solvents are ethers such as tetrahydrofurane or diethylene glycol dimethyl ether (diglyme). The solvent in which the reduction is carried out may be the same as that in which the boron hydride is dissolved, but can also be different therefrom.

The reduction which may be carried out within a wide range of temperature. The reduction may be carried out at room temperature or at a slightly elevated temperature. While secondary amines react with diborane and lactams with diborane and Lewis acid preferably at a slightly elevated temperature (40° to 60° C), the reduction with complex borohydrides and Lewis acids, in particular with imides, often proceeds very favourably in the temperature range of from 0° to 20° C. If somewhat longer reaction times are accepted, it is also possible to carry out the reduction in the cold. The duration of the reduction depends on the reaction components used and on the temperatures selected.

In a preferred method of the process of the invention, the 5-sulphamoylbenzoic acid derivatives of the formula II are first introduced together with the Lewis acid, in an inert solvent and then a solution of the complex borohydride or, if appropriate, a suspension of the complex borohydride in the same or a different solvent is added at room temperature and the whole is stirred for a short time. The complex borohydride can also be added directly in solid form. In order to accelerate the reaction, it may also be carried out at elevated temperature or the mixture may be heated to 50° to 80° C for about 1 hour after completion of the addition of the reducing agent.

Another method comprises first introducing the substance to be reduced together with the complex borohydride and then adding the Lewis acid at room temperature. Sodium borohydride is particularly suitable as the complex borohydride. Here too, it may be advantageous, to achieve a faster conversion, to heat the mixture to 40°–70° C for about 1 hour after the end of the addition of the Lewis acid. With the aid of thin layer chromatography it is possible to follow the progress of the reaction by the appearance of the intensive light-blue fluorescence (in the region of 366 nm) of the resulting compounds of the formula I. In the reduction according to the invention it is possible that double bonds which may be present in the group A may be reduced simultaneously.

The end products can be isolated in several ways. A preferred method of working up consists in adding water and small quantities of an acid in order to free the solution of the reaction product from any reducing agent which may still be present and then precipitating the resulting 5-sulfamoylbenzoic acid esters by adding a non-solvent. When diethylene glycol dimethyl ether is used, a particularly suitable non-solvent is water. The resulting 5-sulfamoylbenzoic acid esters of the formula I generally crystallize almost quantitatively with high purity.

Optionally, it may be necessary subsequently to liberate substituents which are present in the radical X of the sulfamoylbenzoic acid derivatives of the general formula I and which are protected by protective groups. For example, the p-hydroxyl group is obtained by saponifying the corresponding acetates.

It is also possible to obtain the 5-sulfamoylbenzoic acids of the formula I directly by partially concentrating the reaction mixture after decomposition of the excess of reducing agent, adding a dilute base and, if appropriate, heating for a short time. Sodium hydroxide solution, for example, may be used as the base. In this case, the 5-sulfamoylbenzoic acids of the formula I can be isolated directly in the form of their salts. The free acids are obtained by acidification. Owing to the smooth course of the formation of the 3-imido- or 3-amido-5-sulfamoylbenzoic acid derivatives of the formula II, the novel 5-sulfamoylbenzoic acid derivatives of the formula I are obtained according to method (a) with high purity and with a high space-time yield.

The reduction can be carried equally successfully with imides or amides if the C—C chain contains substituents which are split off easily under formation of a carbon-carbon double bond. Thus, for example, the 3-pyrroline derivatives of the formula I in which A represents a

group, are obtained when using 2-bromosuccinic acid as the starting material for the reactant of the formula VIII.

The 3-pyrroline derivatives can be modified chemically in known manner, for example they may be hydrogenated catalytically to give the sulfamoylbenzoic acid derivatives of the formula I in which A represents an ethylene group and with a heterocyclic substituent in the 3-position, or they may be subjected to the usual addition reactions.

The 5-halogenosulfamoylbenzoic acid derivatives of the formula III required for method (b) may be obtained in various ways, for example from the aminobenzoic acid derivatives of the formula XX

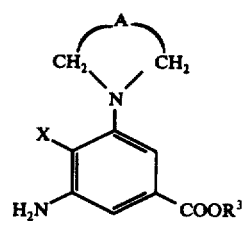

according to the reaction sequence described by Meerwein in J. pr.[2] 152, 251 (1939) or DBP 859,461.

The halogenosulfamoylbenzoic acid derivatives are reacted in known manner with amines of the formula

to give the end products of the formula I. The aminobenzoic acid derivatives of the formula XX are obtained in various ways, for example from the amino-nitrobenzoic acid derivatives of the formula XXI, which are known from literature, according to the reaction scheme

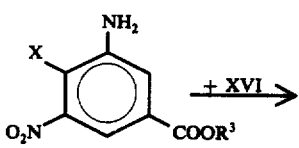

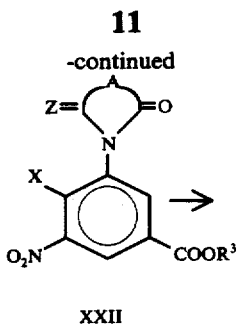

XXII

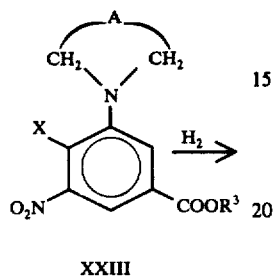

XXIII by reacting the compounds with carboxylic acid derivatives of the formula XVI as described above and subsequently reducing the resulting compounds of the formula XXII by means of boron hydrides or complex borohydrides in the presence of Lewis acids to give the nitrobenzoic acid esters XXII. The nitro group is then reduced, advantageously by catalytic hydrogenation in the presence of Raney nickel or by other conventional reduction methods.

The compound XX can be prepared in a particularly advantageous manner as follows:

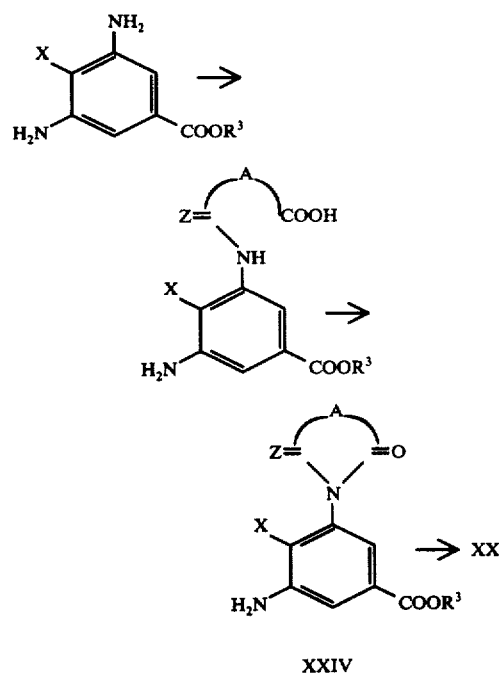

XXIV

In the reduction of the 3-amido- or 3-imido-compounds of the formulae XXIII and XXIV, the same conditions can be used as those described under method (a). In this respect it is surprising that the reduction proceeds specifically also in the presence of a nitro group.

The compounds of the general formula IV used in method (c) are accessible in various ways.

For example, compounds in which D in formula IV represents a $CH_2OH-$ group are obtained from carboxylic acid derivatives of the formula I by means of an excess of reducing agent.

This reaction can be observed as a side-reaction when treating according to method (a) imido- or amido-derivatives of the formula II at too high a temperature for a prolonged period of time with an excess of reducing agent. Thus, according to method (c), it is possible to reconvert the compounds of the formula IV which have been reduced too far into the desired compounds of the formula I by treatment with oxidizing agents.

Conversion of the compounds of the formula IV into the final products of the formula I is effected according to the nature of the substituent D. If D represents a $CH_2$-halogeno group, a $CH_2OCOCH_3$ group or a $CH=O$ group, the end products are obtained by oxidation, as already described. If D represents a nitrile group, the amides are formed on alkaline hydrolysis and may subsequently be converted into the free carboxylic acids, for example by further hydrolysis. Or, the reaction of the nitriles with alcoholic hydrochloric acid gives the imino-esters which can be converted by hydrolysis into the ester compounds, and, if desired, also into the corresponding carboxylic acids.

The sulfamoylbenzoic acid derivatives of the formula V, used in method (d), are accessible in various ways, for example from the sulfamoylbenzoic acid derivatives of the formula XIX

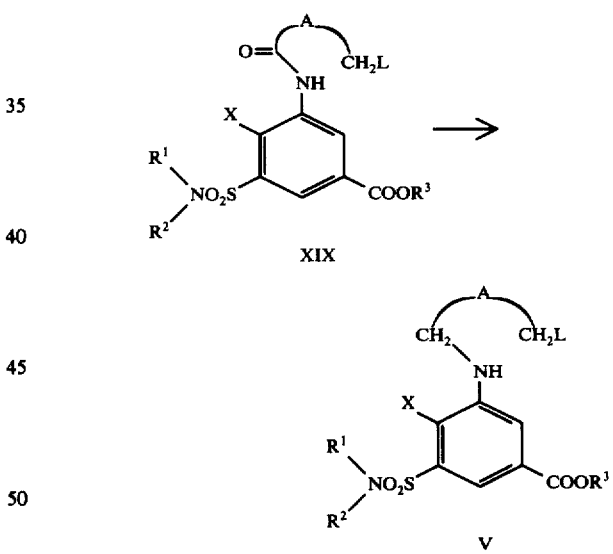

by reducing the amide group with boron hydrides alone or complex borohydrides in the presence of Lewis acids in the manner already described. It is surprising in this reduction that the amide group is reduced without the "leaving group" L being affected. As "leaving group" L, there may be used preferably halogen, OH, active ester groups such as o-tosyl, trialkylammonium or pyridinium groups.

The cyclization of the compounds of the formula V, under elimination of HL, may be carried out under basic or acid conditions. If, for example, L represents a halogen atom, preferably chlorine or bromine, cyclization is effected, for example by treatment with alkali. In an acid medium, the cyclization is carried out according to Ber. dtsch. chem. Ges. 42, 3427 (1909) (Summary in Chem. Rev. 63. 55 (1963)). Thereby, the salts of the carboxylic acids of the formula I ($R^3$ = H) are formed. As bases which may be used in the separation reaction, there may be mentioned triethylamine, alkali metal hydroxides, N,N-dimethylaniline or alkali metal acetate.

The compounds of the invention may also be prepared starting from 3-amino-compounds of the formula XV or XI by reaction with compounds of the formula L—$CH_2$—A—$CH_2$L, whereby both "leaving groups" L are cyclisized with the 3-amino group of XV or XI under separation of 2 moles of HL to compounds of the formula I of XIV.

For this purpose, the compounds XV or XI are reacted in organic solvents, for example acetone, dimethylformamide, ethanol, or mixtures of such solvents with an excess of compounds of the formula L—$CH_2$—A—$CH_2$—L, suitably by heating for several hours to days under reflux. It is of advantage, if L represents bromine or chlorine atome, to add an excess of an alkali metal iodide to the reaction mixture. In some cases, an auxiliary base, for example pyridine, triethylamine, $NaHCO_2$ or Na-acetate, accelerates the reaction.

The sulfamoylbenzoic acid derivatives of the formula VI used in method (e) are accessible by various processes, for example from the compounds of the formula V in which A represents in this case a single bond or an optionally substituted methylene group or ethylene group, and L represents a halogen atom, preferably chlorine or bromine, by reaction with formaldehyde and hydrohalic acids or by a further reaction with ω-halogenocarboxylic acids under formation of an amido compound of the formula XXV which is reduced in the manner already described (c.f. the following reaction scheme).

react compounds of the formula VI with nucleophils such as primary amines, $NH_3$ or $H_2S$, whereby the ring in the 3-position is closed under incorporation of a further heteroatom N or S.

The compounds of the formula VII used in method (f) are obtained from 3-amino-5-sulfamoylbenzoic acid derivatives of the formula XV by reacting them in the usual manner with 2,5-dimethoxytetrahydrofuranes of the formula

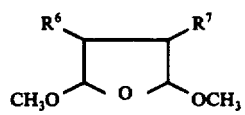

in which $R^6$, and $R^7$ have the meanings given above. Reduction of the resulting pyrrolo-compounds VII is effected preferably by catalytic hydrogenation with the catalysts usually employed for such purposes.

The benzoic acid derivatives of the formula VIII used in method (g) are accessible by various methods. The reaction is particularly simple to carry out when starting from the sulfamoylbenzoic acid derivatives of the following formula

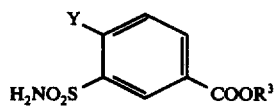

which are unsubstituted in the sulfamoyl group and known from literature and using one of the various condensation methods largely known from literature.

The following literature is cited by way of example:

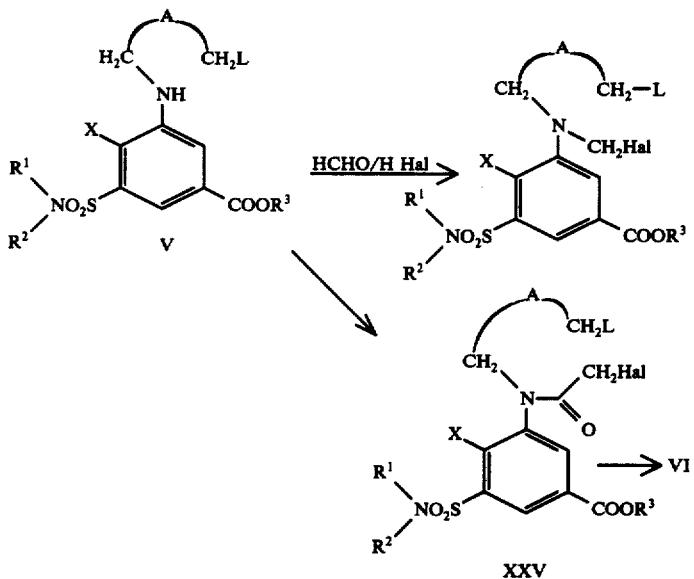

The subsequent cyclization is effected in a manner known from literature, for example according to the method described by Wurtz by the reaction of the compounds of the formula VI with metallic sodium or by the action of Zn on the boiling alcoholic solution, as described in J. prakt. Chem. /2/36, 300 (1887). This method is particularly suitable for the preparation of 4-membered and 5-membered rings in the 3-position of the compounds of the formula I. It is also possible to J. Org. Chem. 25 (1960), 352–356; Zh. Org. Khim 8 (1972), 286–291; Liebigs Ann. Chem. 750 (1971), 42; Zh. Org. Khim. 6 (1970), 9,1855; B. 94 (1961), 2731-2737; Ang. Ch. 78 (1966), 147–148; Ang. Ch. 80 (1968), 281–282; B. 97 (1964), 483–489; B. 96 (1963), 802–812; J. Org. Chem. 27 (1962), 4566–4570; Ang. Ch. 74 (1962), 781–782, and Doklady Akad, SSSR 145 (1962), 584.

As compounds of the general formula VIII, there may be used according to the invention, for example, the following derivatives:

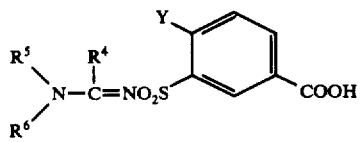

| Compound No. | R⁴ | R⁵ | R⁶ | Y |
|---|---|---|---|---|
| 1 | H | $CH_3$ | $CH_3$ | Cl |
| 2 | $CH_3$ | $CH_3$ | $CH_3$ | Cl |
| 3 | H | $C_2H_5$ | $C_2H_5$ | Cl |
| 4 | $C_4H_9$ | $CH_3$ | $CH_3$ | Cl |
| 5 | H | $CH_3$ | $CH_3$ | F |
| 6 | H | $CH_3$ | $CH_3$ | Br |
| 7 | $CH_3$ | —$CH_2$—$CH_2$—$CH_2$—$CH_2$—$CH_2$— | | Cl |
| 8 | —$CH_2$—$CH_2$—$CH_2$— | | $CH_3$ | Cl |

The compounds of the formula VIII are prepared according to the above methods described in literature or analogously to these. Instead of the above-mentioned acids, there may also be used, for example the corresponding methyl or ethyl esters.

Nitration of the benzoic acid derivatives of the formula VIII can be effected in various ways. For example, the benzoic acid derivatives may be introduced into one of the conventional nitrating mixtures for the nitration of inert aromatic substances (cf. manual "Organicum", page 288, Edition 1967). The process may also be carried out by dissolving the benzoic acid derivatives of the formula VIII in oleum and controlling the nitration by dropwise addition of nitric acid.

It is surprising that it is possible to nitrate the benzoic acid derivatives of the general formula VIII merely by the introduction of the protective group B into the sulfonamide radical, without modification of other groups in the molecule.

The reaction temperature is relatively low; preferably, temperatures in the range of from 55° to 70° C are maintained.

It is advantageous first to introduce a nitrating acid of oleum and fuming nitric acid, then to add the substance and to heat the reaction mixture to 55° – 60° C.

The course of the nitration can be followed by thin-layer chromatography. Isolation of the final products is carried out in the usual manner, for example by pouring the reaction mixture onto ice and separating by filtration the cristals that have precipitated.

For the nitration, acids or esters of the general formula VIII, in which the radicals Y, B and $R^3$ have the meanings given above, may be used. In the nitration of the esters of the formula VIII, also the acids of the formula IX (with $R^3 =$ H) are obtained in small amounts in addition to the esters.

The mixture can be split in the usual manner, for example by treatment with aqueous sodium carbonate.

The compounds of the formula IX so obtained, in which $R^3$ is hydrogen, are then esterified in the usual manner.

For esterifying the carboxyl group, for example the carboxylic acid is converted into its acid chloride which, upon addition of alcohols, yields the corresponding esters of the formula IX.

Suitable alcohols for the esterification are, in particular lower alkyl alcohols of 1 to 4 carbon atoms such as methanol, ethanol, propanol, butanol, isopropanol or isobutanol.

It is of advantage to use them in a 5- to 20-fold molar excess or to use them simultaneously as solvent.

In the next step, the esters of the formula IX are converted by reaction with compounds of the formula XH into compounds of the formula X.

It has been found that, surprisingly, compounds of the general formula IX, in which $R^3$ is alkyl, can be reacted under anhydrous conditions with good yields with compounds of the general formula XH.

As compounds of the formula XH, there may be used, for example phenol, 4-methylphenol, 3-methylphenol, 2-methylphenol, 4-chlorophenol, 3-trifluoromethylphenol, 3,5-dimethylphenol, 2,4-dimethylphenol, 4-methoxyphenol, 3-methoxyphenol, 4-propylphenol, thiophenol and the thiophenols substituted in the same manner as the phenols, N-methylaniline, benzenesulfinic acid, pyrrolidine, N-methyl-piperazine, 5-methyl-2-mercapto-1,3,4-thiadiazole or 1-methyl-5-mercapto-1,2,3,4-tetrazole. Any additionally present functional groups in XH as well as other OH-groups, $NH_2$- or mercapto-groups are blocked by the usual protective groups, for example by acylation.

Compounds of the general formula $HOR^4$ and $HSR^4$, in which the radical $R^4$ has the meanings given above, are of great importance. Among them, the thiophenol and phenol derivatives, which may be substituted as already indicated, are of particular importance.

The reaction may be carried out without solvent, but it is more advantageous to operated in the presence of a solvent. Particularly suitable solvents are organic solvents such as ether and tert. carboxamides, in particular diglyme, dimethylformamide or hexamethylphosphoric acid-tris-amide (HMPT).

The compounds X-H are used as such in the presence of bases or in the form of their alkali metal salts or alkaline earth metal salts. As bases, alcoholates or alkali metal amides are used.

The thiophenol and phenol derivatives are reacted in the form of their anions; among these, the alkali metal salts, especially the sodium and potassium salts, are particularly suitable.

The reaction may be carried out in the presence or in the absence of a solvent. Without solvent, the components are heated, for example to temperatures in the range of from 100° to 200° C, preferably 140° to 180° C. The resulting products can be isolated in the usual manner, for example by dissolving the molten products in a solvent and subsequently precipitating them by the addition of water or of an organic non-solvent.

The reaction with phenolates or thiophenolates in solvents at temperatures in the range of from 100° to 200° C, preferably from 120° to 160° C, however, is particularly advantageous.

As solvents, there may be used organic solvents, in particular tertiary carboxyamides, polyethers or high-boiling solvents such as HMPT or tetramethylenesulfone. Particularly advantageous is the reaction of the esters of the formula IX in tertiary carboxamides, for example dimethylformamide or dimethylacetamide. Depending on the reaction temperature selected, the reaction is completed after 1 to 6 hours.

The isolation of the final products of the formula X is effected in the usual manner; for example, the inorganic salts are first filtered off and the reaction product is then precipitated by the addition of a non-solvent or the reaction mixture is poured into water or onto ice and the reaction product that has precipitated is isolated.

The compounds of the formula X, in which $SOR^4$ or $SO_2R^4$ is in the 4-position, are obtained from the corresponding compounds of the formula X with $SR^4$ by oxidation according to methods known from literature. For example, the S-oxides are obtained by oxidation with per-acetic acid in dimethylformamide at low temperatures, while the S-dioxides are formed upon addition of an excess of oxidizing agent at more elevated temperatures.

The reduction of the nitro group in benzoic acid derivatives of the formula X may be effected in the usual manner, for example by catalytical hydrogenation. As catalyst, preferably Raney nickel or the usual noble metal catalysts such as palladium on charcoal or platinum oxide are used (cf. for example Organikum, pages 271–277, pages 507–510).

As solvents for the reduction, preferably organic solvents such as methanol or ethanol, ethyl acetate, dioxane or other polar solvents, in particular amides such as dimethylformamide, dimethylacetamide or HMPT, are used.

Hydrogenation is effected at room temperature and under normal pressure or at an elevated temperature and increased pressure, for example at 50° C and 100 atmospheres gauge in an autoclave.

The 3-imidobenzoic acid derivatives of the general formula XIII are accessible in various ways. For example, they may be obtained by reacting the amino compounds XI with dicarboxylic acid derivatives of the general formula XII which are capable of forming imides. The reaction is carried out in a manner analogous to the reaction described under method (a) of the compounds XV and XVI to compounds to the formula II.

The reaction can be easily followed by thin-layer chromatography, since the amino compounds XI fluoresce at 366 mµ, while the compounds obtained show no fluorescence.

The amido-compounds of the formula XIII, in which Z represents 2 hydrogen atoms, are prepared in a manner analogous to that for the compounds II, in which Z stands for 2 H-atoms, as described under method (a).

The carboxylic acid derivatives of the formula XII correspond to the above-described compounds of the formula XVI.

In the reduction of compounds of the formula XIII, the benzoic acid derivatives of the general formula XIV, which are substituted heterocyclically in the 3-position, are obtained. In order to obtain particularly pure products with high yield, it is also in this case of advantage to use in the reduction the benzoic acid esters of the formula XIII. The reduction is effected as described under method (a).

The 5-sulfamoylbenzoic acids of the formula I ($R^3$ = H) of the invention are obtained by alkaline hydrolysis of the compounds of the general formula XIV by heating these compounds of the formula XIV for several hours in a sodium or potassium hydroxide solution on the steam bath. Thereby, the ester is saponified and the protective group B as well as any other protective groups present are split off.

The 5-sulfamoylbenzoic acids of the formula I ($R^3$ = H) may also be obtained directly by partially concentrating the reaction mixture after destruction of the excess of reducing agent, adding a base and heating for a prolonged period of time. As base, for example sodium hydroxide solution may be used. The 5-sulfamoylbenzoic acids of the formula I can so be isolated directly in the form of their salts. The free acids are obtained by acidification. Surprisingly, the 3-amidobenzoic acid derivatives of the general formula XIII in which X means phenoxy, benzyl or phenylthio, can be nitrated at low temperatures with fuming nitric acid at the 4-position of the phenoxy, benzyl or phenylthio-group without affecting any other group in the molecule. This process is of particular interest in synthesizing compounds of formula I in which X stands for the 4-nitrophenoxy, 4-amino-phenoxy, 4-nitrobenzyl, 4-aminobenzyl, 4-nitrophenylthio and 4-aminophenylthio-group.

It is also possible to introduce the protective group B in a later reaction stage, for example into compounds of the formulae IX, X, XI or XIII, in which B then represents 2 hydrogen atoms, and to obtain in this way compounds of the formula XIV, in which R' may also be replaced by R.

Subsequent to the methods listed under (a) to (g), any double bonds which may be present in the compounds of the formula I of the invention may be hydrogenated in the customary manner, using catalytical hydrogenation. Conversely, it is also possible subsequently to introduce double bonds by elimination reactions, for example by separating hydrogen halide from halogenated compounds, by separating water from hydroxy compounds and by other conventional splitting reactions.

If free carboxylic acids of the formula I are first obtained when suitable starting compounds have been used, they may be converted in the usual manner into esters. For this purpose, alcohols of the formula $R^3OH$ or their functional derivatives are used or esterification is carried out in some other manner known from literature. Conversely, if carboxylic acid esters of the general formula I are first obtained, they may be converted into the corresponding free carboxylic acids. Hydrolysis may be used in particular for this purpose or, in suitable cases, even hydrogenolysis or other elimination reactions. Thus, it is possible, for example, to split alkyl esters by alkaline hydrolysis, aralkyl esters, in particular p-nitrobenzyl esters, by hydrogenolysis or the tert.-butyl esters by elimination of isobutylene upon treatment with trifluoroacetic acid.

The free carboxylic acids may be converted into their physiologically tolerated salts by reacting them with appropriate bases such as alkali metal, alkaline earth metal or ammonium hydroxides or carbonates. Finally, it is possible to obtain the compounds of the formula I of the invention by separating, in the last reaction stage, one of the customary protective groups for the hydroxyl, amino or mercapto groups, whereby, for example acylated hydroxyl groups are hydrolyzed in the customary manner. The protective groups of hydroxyl, amino or mercapto groups are required especially in the preparation of the starting materials of the formula II, in order to prevent acylation with carboxylic acid derivatives of the formula XII at undesired positions. In this case, the reduction according to the invention by method (a) is often carried out with the protected hydroxy, amino or mercapto compounds and the separation of the protective group is only carried out, as described above, after the reduction. However, even in the other methods it may be suitable to block reactive substituents which are split off in the last reaction stage.

A large number of highly active pharmaceutical agents can be prepared by the process of the invention, especially diuretics and saluretics, some of which are specified hereinafter:

4-phenoxy-3(1-aziridinyl)-5-sulfamoylbenzoic acid
4-phenoxy-3(1-azetidinyl)-5-sulfamoylbenzoic acid
4-phenoxy-3(1-pyrrolidinyl)-5-sulfamoylbenzoic acid
4-chloro-3(1-pyrrolidinyl)-5-sulfamoylbenzoic acid
4-(4'-chlorophenoxy)-3(1-pyrrolidinyl)-5-sulfamoylbenzoic acid
4-(4'-methylphenoxy)-3(1-pyrrolidinyl)-5-sulfamoylbenzoic acid
4-(3'-methylphenoxy)-3(1-pyrrolidinyl)-5-sulfamoylbenzoic acid
4-(2'-methylphenoxy) -3(1-pyrrolidinyl)-5-sulfamoylbenzoic acid
4-(4'-nitrophenoxy)-3(1-pyrrolidinyl)-5-sulfamoylbenzoic acid
4-(4'-sulfamoylphenyl)-3(1-pyrrolidinyl)-5-sulfamoylbenzoic acid
4-(2',4'-dimethylphenoxy)-3(1-pyrrolidinyl)-5-sulfamoylbenzoic acid
4-(3',5'-dimethylphenoxy)-3(1-pyrrolidinyl)-5-sulfamoylbenzoic acid
4-(4'-hydroxyphenoxy)-3(1-pyrrolidinyl)-5-sulfamoylbenzoic acid
4-(4'-methoxyphenoxy)-3(1-pyrrolidinyl)-5-sulfamoylbenzoic acid
4-(4'-trifluoromethylphenoxy)-3(1-pyrrolidinyl)-5-sulfamoylbenzoic acid
4-(3'-trifluoromethylphenoxy)-3(1-pyrrolidinyl)-5-sulfamoylbenzoic acid
4-(3'-trifluoromethylphenoxy)-3(1-pyrrolidinyl)-5-sulfamoylbenzoic acid
4-(4'-aminophenoxy)-3(1-pyrrolidinyl)-5-sulfamoylbenzoic acid
4-(4'-dimethylaminophenoxy)-3(1-pyrrolidinyl)-5-sulfamoylbenzoic acid
4-(4'-sulfamoylphenoxy)-3(1-pyrrolidinyl)-5-sulfamoylbenzoic acid
4-phenylthio-3(1-pyrrolidinyl)-5-sulfamoylbenzoic acid
4-(4'-methylphenylthio)-3(1-pyrrolidinyl)-5-sulfamoylbenzoic acid
4-(4'-chlorophenylthio)-3(1-pyrrolidinyl)-5-sulfamoylbenzoic acid
4-phenylsulfinyl-3(1-pyrrolidinyl)-5-sulfamoylbenzoic acid
4-(4'-methylphenylsulfinyl)-3(1-pyrrolidinyl)-5-sulfamoylbenzoic acid
4-phenylsulfonyl-3(1-pyrrolidinyl)-5-sulfamoylbenzoic acid
4-(4'-methylphenylsulfonyl)-3(1-pyrrolidinyl)-5-sulfamoylbenzoic acid
4-n-butoxy-3(1-pyrrolidinyl)-5-sulfamoylbenzoic acid
4-n-pentoxy-3(1-pyrrolidinyl)-5-sulfamoylbenzoic acid
4-trichloromethyl-3(1-pyrrolidinyl)-5-sulfamoylbenzoic acid
4-trifluoromethyl-3(1-pyrrolidinyl)-5-sulfamoylbenzoic acid
4-(N-methyl-N-phenylamino)-3(1-pyrrolidinyl)-5-sulfamoylbenzoic acid
3,4-di(1-pyrrolidinyl)-5-sulfamoylbenzoic acid
3(1-pyrrolidinyl)-4(1-methylpiperazinyl)-5-sulfamoylbenzoic acid
4-benzyl-3(1-pyrrolidinyl)-5-sulfamoylbenzoic acid
4-(4'-methylbenzyl)-3(1-pyrrolidinyl)-5-sulfamoylbenzoic acid
4-(4'-methoxybenzyl)-3(1-pyrrolidinyl)-5-sulfamoylbenzoic acid
4-(4'-chlorobenzyl)-3(1-pyrrolidinyl)-5-sulfamoylbenzoic acid
4-(4'-aminobenzyl)-3(1-pyrrolidinyl)-5-sulfamoylbenzoic acid
4-methyl-3(1-pyrrolidinyl)-5-sulfamoylbenzoic acid
4-n-butyl-3(1-pyrrolidinyl)-5-sulfamoylbenzoic acid
4-chloro-3(3-methyl-1-pyrrolidinyl)-5-sulfamoylbenzoic acid
4-phenoxy-3(3-methyl-1-pyrrolidinyl)-5-sulfamoylbenzoic acid
4-(4'-chlorophenoxy)-3(3-methyl-1-pyrrolidinyl)-5-sulfamoylbenzoic acid
4-(4'-methylphenoxy)-3(3-methyl-1-pyrrolidinyl)-5-sulfamoylbenzoic acid
4-(3'-methylphenoxy)-3(3-methyl-1-pyrrolidinyl)-5-sulfamoylbenzoic acid
4-(2'-methylphenoxy)-3(3-methyl-1-pyrrolidinyl)-5-sulfamoylbenzoic acid
4-(2',4'-dimethylphenoxy)-3(3-methyl-1-pyrrolidinyl)-5-sulfamoylbenzoic acid
4-(3',5'-dimethylphenoxy)-3(3-methyl-1-pyrrolidinyl)-5-sulfamoylbenzoic acid
4-(4'-hydroxyphenoxy)-3(3-methyl-1-pyrrolidinyl)-5-sulfamoylbenzoic acid
4-(4'-methoxyphenoxy)-3(3-methyl-1-pyrrolidinyl)-5-sulfamoylbenzoic acid
4-(4'-nitrophenoxy)-3(3-methyl-1-pyrrolidinyl)-5-sulfamoylbenzoic acid
4-(4'-aminophenoxy)-3(3-methyl-1-pyrrolidinyl)-5-sulfamoylbenzoic acid
4-(4'-dimethylaminophenoxy)-3(3-methyl-1-pyrrolidinyl)-5-sulfamoylbenzoic acid
4-(3'-trifluoromethylphenoxy)-3(3-methyl-1-pyrrolidinyl)-5-sulfamoylbenzoic acid
4-(4'-propylphenoxy)-3(3-methyl-1-pyrrolidinyl)-5-sulfamoylbenzoic acid
4-phenylthio-3(3-methyl-1-pyrrolidinyl)-5-sulfamoylbenzoic acid
4-(4'-methylphenylthio)-3(3-methyl-1-pyrrolidinyl)-5-sulfamoylbenzoic acid
4-(4'-chlorophenylthio)-3(3-methyl-1-pyrrolidinyl)-5-sulfamoylbenzoic acid
4-phenylsulfinyl-3(3-methyl-1-pyrrolidinyl)-5-sulfamoylbenzoic acid
4-(4'-methylphenylsulfinyl)-3(3-methyl-1-pyrrolidinyl)-5-sulfamoylbenzoic acid
4-phenylsulfonyl-3(3-methyl-1-pyrrolidinyl)-5-sulfamoylbenzoic acid
4-(4'-methylphenylsulfonyl-3(3-methyl-1-pyrrolidinyl)-5-sulfamoylbenzoic acid
4-n-butoxy-3(3-methyl-1-pyrrolidinyl)-5-sulfamoylbenzoic acid
4-n-pentoxy-3(3-methyl-1-pyrrolidinyl)-5-sulfamoylbenzoic acid
4-trichloromethyl-3(3-methyl-1-pyrrolidinyl)-5-sulfamoylbenzoic acid 4-trifluoromethyl-3(3-methyl-1-pyrrolidinyl)-5-sulfamoylbenzoic acid 4-(N-methyl-N-phenylamino)-3(3-methyl-1-pyrrolidinyl)-5-sulfamoylbenzoic acid 4-benzyl-3(3-methyl-1-pyrrolidinyl)-5-sulfamoylbenzoic acid 4-(4'-methylbenzyl)-3(3-methyl-1-pyrrolidinyl)-5-sulfamoylbenzoic acid 4-(4'-methoxybenzyl)-3(3-methyl-1-pyrrolidinyl)-5-sulfamoylbenzoic acid 4-(4'-chlorobenzyl)-3(3-methyl-1-pyrrolidinyl)-5-sulfamoylbenzoic acid 4-(4'-aminobenzyl)-3(3-methyl-1-pyrrolidinyl)-5-sulfamoylbenzoic acid 4-methyl-3(3-methyl-1-pyrrolidinyl)-5-sulfamoylbenzoic 4-n-butyl-3(3-methyl-1-pyrrolidinyl)-5-sulfamoylbenzoic acid 4-phenoxy-3(3,3-dimethyl-1-pyrrolidinyl)-5-sulfamoylbenzoic acid 4-(4'-methylphenoxy)-3(3,3-dimethyl-1-pyrrolidinyl)-5-sulfamoylbenzoic acid 4-benzyl-3(3,3-dimethyl-1-pyrrolidinyl)-5-sulfamoylbenzoic acid 4-phenoxy-3(3,4-dimethyl-1-pyrrolidinyl)-5-sulfamoylbenzoic acid 4-(4'-chlorophenoxy)-3(3,4-dimethyl-1-pyrrolidinyl)-5-sulfamoylbenzoic acid 4-(4'-methylphenoxy)-3(3,4-dimethyl-1-pyrrolidinyl)-5-sulfamoylbenzoic acid 4-benzyl-3(3,4-dimethyl-1-pyrrolidinyl)-5-sulfamoylbenzoic acid 4-phenoxy-3-(3-pyrrolin-1-yl)-5-sulfamoylbenzoic acid 4-(4'-methylphenoxy)-3(3-pyrrolin-1-yl)-5-sulfamoylbenzoic acid 4-(4'-chlorophenoxy)-3(3-pyrrolin-1-yl)-5-sulfamoylbenzoic acid 4-phenoxy-3(3-phenyl-1-pyrrolidinyl)-5-sulfamoylbenzoic acid 4-(4'-methylphenoxy)-3(3-phenyl-1-pyrrolidinyl)-5-sulfamoylbenzoic acid 4-phenoxy-3(3-chloro-1-pyrrolidinyl)-5-sulfamoylbenzoic acid 4-phenoxy-3(1-piperidyl)-5-sulfamoylbenzoic acid 4-(4'-chlorphenoxy)-3(1-piperidyl)-5-sulfamoylbenzoic acid 4-(4'-methylphenoxy)-3(1-piperidyl)-5-sulfamoylbenzoic acid 4-(3',5'-dimethylphenoxy)-3(1-piperidyl)-5-sulfamoylbenzoic acid 4-(4'-hydroxyphenoxy)-3(1-piperidyl)-5-sulfamoylbenzoic acid 4-(4'-methoxyphenoxy)-3(1-piperidyl)-5-sulfamoylbenzoic acid 4-(4'-nitrophenoxy)-3(1-piperidyl)-5-sulfamoylbenzoic acid 4-(4'-aminophenoxy)-3(1-piperidyl)-5-sulfamoylbenzoic acid 4-(3'-trifluoromethylphenoxy)-3(1-piperidyl)-5-sulfamoylbenzoic acid 4-(4'-propylphenoxy)-3(1-piperidyl)-5-sulfamoylbenzoic acid 4-n-butoxy-3(1-piperidyl)-5-sulfamoylbenzoic acid 4-n-pentoxy-3(1-piperidyl)-5-sulfamoylbenzoic acid 4-phenylthio-3(1-piperidyl)-5-sulfamoylbenzoic acid 4-phenylsulfinyl-3(1-piperidyl)-5-sulfamoylbenzoic acid 4-phenylsulfonyl-3(1-piperidyl)-5-sulfamoylbenzoic acid 4-trifluoromethyl-3(1-piperidyl)-5-sulfamoylbenzoic acid 4-(N-methyl-N-phenylamino)-3(1-piperidyl)-5-sulfamoylbenzoic acid 4-benzyl-3(1-piperidyl)-5-sulfamoylbenzoic The pharmaceutically active compounds prepared by the process of the invention, also include, by way of example, the corresponding 5-N-methyl-, 5-N-ethyl-, 5-N-methoxymethyl- and 5-N-butoxymethylsulfamoylbenzoic acids as well as the corresponding benzoic acid methyl-, ethyl-, benzyl- and tert.-butyl esters thereof.

The sulfamoylbenzoic acid derivatives of the formula I of the invention and their physiologically tolerated salts are highly active diuretics and saluretics which can be used as pharmaceutical agents in human and veterinary medicine.

The compounds of the invention are administered enterally, for example perorally or parenterally (injection into the vascular system, for example intravenous injection or intramuscular injection or subcutaneous injection and the like) in dosages of 0.5 to 100 mg, in capsules, dragées, tablets or solutions with various additives. They are suitable for the treatment of edematous diseases such as edemas caused by certain cardiac, renal or hepatic conditions and other similar disorders of the water balance and electrolyte metabolism. The average daily dosis to patients lies between 2 and 10 mg, i.e. 0.025 to 0.15 mg/kg pro die. The compounds may be administered, particularly to human patients, as such alone or in combination with other substances having a salidiuretic action, but another mode of action, or they may be administered with various other medicaments, separately from them, alternately with them or in combination with them. In this respect, there may be mentioned SPIRONOLACTON, TRIAMTEREN, AMILORID and other $K^+$-retaining compounds, alternatingly with long-acting salidiuretics of the type of CHLORTHALIDON or others, together with, or separately from, the potassium-containing compounds (salts or the like) which replace the loss of $K^+$ which is observed in salidiuresis.

The following Examples illustrate the invention.

EXAMPLE 1

3-Nitro-4-phenoxy-5-sulphamylbenzoic acid methyl ester 34 g (~0.1 mol) of 3-nitro-4-phenoxy-5-sulphamylbenzoic acid are dissolved in 150 ml of methanol and are heated to the boil. 5.4 ml of concentrated $H_2SO_4$ are then added slowly dropwise and the mixture is heated at reflux temperature for 10 hours. On cooling, 3-nitro-4-phenoxy-5-sulphamylbenzoic acid methyl ester crystallises.

It can be recrystallised from methanol/acetone.
Melting point: 181° – 182° C.

EXAMPLE 2

3-Amino-4-phenoxy-5-sulphamylbenzoic acid methyl ester 35 g (~0.1 mol) of 3-nitro-4-phenoxy-5-sulphamylbenzoic acid methyl ester are suspended in 150 ml of methanol and are hydrogenated with Raney nickel (5–10%) in an autoclave at 40° – 50° and 100 atmospheres gauge. The precipitated amino compound is dissolved by the addition of acetone on a steambath and the Raney nickel is removed by filtration.

On cooling, 3-amino-4-phenoxy-5-sulphamylbenzoic acid methyl ester crystallises out cleanly.

Melting point: 179° C.

EXAMPLE 3

3-N-Succinimido-4-phenoxy-5-sulphamylbenzoic acid methyl ester 16.1 g (0.05 mol) of 3-amino-4-phenoxy-5-sulphamylbenzoic acid methyl ester are dissolved in 150 ml of absolute dioxane and the solution is heated to the boil.

A solution of 11.6 g (0.075 mol) of succinic acid dichloride in 50 ml of absolute acetone and a solution of 8 ml of pyridine in 50 ml of absolute acetone are then added dropwise at the same rate but separately, with good stirring, and the mixture is heated under reflux. The reaction is complete after about 2 hours. The mixture is concentrated and the residual oil is taken up in a little methanol. 3-N-Succinimido-4-phenoxy-5-sulphamylbenzoic acid methyl ester crystallises out after a short time.

Crystallisation is completed by adding a little water.

Recrystallisation is carried out from methanol/acetone.

Melting point: 270°.

EXAMPLE 3a

3-Amino-4-phenoxy-5-sulphamylbenzoic acid methyl ester is fused with a 2-3-fold molar quantity of succinic anhydride, for about 2 hours at 160° - 180° C. On cooling and adding methanol, 3-N-succinimido-4-phenoxy-5-sulphamylbenzoic acid methyl ester crystallises out.

EXAMPLE 4

3-N-Pyrrolidino-4-phenoxy-5-sulphamylbenzoic acid methyl ester 12.3 g (0.03 mole) of 3-N-succinimido-4-phenoxy-5-sulphamylbenzoic acid methyl ester are dissolved or suspended in 100 ml of absolute diglyme. 9 g of boron trifluoride etherate are added direct to this and a solution of 2.4 g (~0.063 mol) of NaBH$_4$ in 80 ml of diglyme is then added dropwise at room temperature and with good stirring. As the reaction proceeds exothermically, it is necessary to cool with ice water. The reaction is normally complete after the dropwise addition and a short period of stirring thereafter.

The excess reducing agent is then decomposed by means of a little water (foaming!), the solution is filtered and about 300 ml of water are added while stirring. The 3-N-pyrrolidino-4-phenoxy-5-sulphamylbenzoic acid methyl ester which has crystallised out is recrystallised from methanol.

Colourless crystals, melting point: 191° - 192°.

NMR data: (CDCl$_3$, 60 MHz, TMS as internal standard) $\delta$ = 1.73 (m; 4H), $\delta$ = 3.26 (m; 4H), $\delta$ = 3.91 (s; 3H), $\delta$ = 5.0 (s; 2H), $\delta$ = 6.6–8.0 (m; 7H) in ppm.

EXAMPLE 5

3-N-Pyrrolidino-4-phenoxy-5-sulphamylbenzoic acid 61 g of 3-N-pyrrolidino-4-phenoxy-5-sulphamylbenzoic acid methyl ester are suspended in 350 ml of 1 N-NaOH and the suspension is heated for one hour on the waterbath. 3-N-Pyrrolidino-4-phenoxy-5-sulphamylbenzoic acid is precipitated from the clear solution by means of 2 N HCl while stirring well. The almost pure crude product can be recrystallised from methanol/water.

Light yellow platelets, melting point: 225° - 227°, with decomposition.

NMR data: (D$_6$-DMSO, 60 MHz, TMS) $\delta$ = 1.67 (quasi-s; 4H), $\delta$ = 3.21 (quasi-s; 4H), $\delta$ = 6.6–8.0 (m; 9H) in ppm.

EXAMPLE 6

3-N-Glutarimido-4-phenoxy-5-sulphamylbenzoic acid methyl ester 16.1 g of 3-amino-4-phenoxy-5-sulphamylbenzoic acid methyl ester are dissolved in 150 ml of absolute dioxane and the solution is heated to the boil. A solution of 16.8 g of glutaric acid dichloride in 50 ml of absolute acetone and a solution of 8 ml of pyridine in 50 ml of absolute acetone are then added dropwise at the same rate, while stirring well, and the mixture is heated under reflux. The reaction is complete after about 3 hours. The mixture is concentrated and the residue is taken up in a little methanol. 3-N-Glutarimido-4-phenoxy-5-sulphamylbenzoic acid methyl ester crystallises out after a short time. It can be recrystallised from glycol monomethyl ether. Colourless crystals, melting point 312° - 314° C, with decomposition.

EXAMPLE 7

3-N-Piperidino-4-phenoxy-5-sulphamylbenzoic acid methyl ester 15 g of 3-N-glutarimido-4-phenoxy-5-sulphamylbenzoic acid methyl ester are suspended in 200 ml of diglyme (diethylene glycol dimethyl ether) and 10 ml of boron trifluoride etherate are added. A solution of 3 g of NaBH$_4$ in 150 ml of diglyme is then added slowly at room temperature with good stirring. The excess reducing agent is then decomposed with a little water, the solution is filtered and 500 ml of water are added, while stirring. The 3-N-piperidino-4-phenoxy-5-sulphamylbenzoic acid methyl ester which has crystallised out can be recrystallised from alcohol.

White crystals, melting point 198° - 199° C.

NMR data: (D$_6$-DMSO, 60 MHz, TMS) $\delta$ = 1.1 (quasi-s; 6H), $\delta$ = 2.86 (quasi-s; 4H), $\delta$ = 3.92 (s; 3H), $\delta$ = 6.7–8.1 (m; 9H) in ppm.

EXAMPLE 8

3-N-Piperidino-4-phenoxy-5-sulphamylbenzoic acid 8 g of 3-N-piperidino-4-phenoxy-5-sulphamylbenzoic acid methyl ester are suspended in 50 ml of 1 N NaOH and the suspension is heated on a steambath until a clear solution is formed. The resulting 3-N-piperidino-4-phenoxy-5-sulphamylbenzoic acid is precipitated with 2 N HCl and is recrystallised from methanol/water.

White crystals, melting point 258° - 260°.

NMR data: (D$_6$-DMSO, 60 MHz, TMS) $\delta$ = 1.08 (quasi-s; 6H), $\delta$ = 2.9 (quasi-s; 4H), $\delta$ = 6.65–8.2 (m; 9H) in ppm.

EXAMPLE 9

3-N-Phthalimido-4-phenoxy-5-sulphamylbenzoic acid methyl ester 16 g of 3-amino-4-phenoxy-5-sulphamylbenzoic acid methyl ester are dissolved in 200 ml of absolute dioxane and the solution is heated to the boil. A solution of 14 ml of phthalic acid dichloride in 50 ml of acetone and a solution of 9 ml of pyridine in 50 ml of acetone are then added dropwise at the same rate, while stirring well. The reaction is complete after 3 hours. The solution is concentrated and the residue is taken up in a little acetone and added dropwise, with good stirring, to a mixture of ice water and 2 N HCl. A light brown precipitate of the 3-N-phthalimido-4-phenoxy-5-sulphamylbenzoic acid methyl ester is thrown down. Recrystallisation from methanol/acetone/H$_2$O gives colourless crystals, melting point 237° - 238° C.

EXAMPLE 10

3-N-Isoindolinyl-4-phenoxy-5-sulphamylbenzoic acid methyl ester 16 g of 3-N-phthalimido-4-phenoxy-5-sulphamylbenzoic acid methyl ester are dissolved or suspended in 150 ml of diglyme and 12 ml of boron trifluoride etherate are added. A solution of 3.6 g of NaBH$_4$ in 100 ml of diglyme is then added dropwise at room temperature and the mixture is stirred for a further one-half hour at 60° C. On adding 400 ml of water, a flocculent mixture of substances separates out. It is boiled up with methanol, during which the 3-N-isoindolinyl-4-phenoxy-5-sulphamylbenzoic acid methyl ester does not dissolve. It is filtered off and recrystallised from n-butanol/DMF.

White needles, melting point: 268° - 272°, with decomposition.

NMR data: (D$_6$-DMSO, 60 MHz, TMS) δ = 3.92 (s; 3H), δ = 4.66 (s; 4H), δ = 6.6–8.1 (m; 13H) in ppm.

EXAMPLE 11

3-N-Isoindolinyl-4-phenoxy-5-sulphamylbenzoic acid 2.5 g of 3-N-isoindolinyl-4-phenoxy-5-sulphamylbenzoic acid methyl ester are suspended in 50 ml of 1 NNaOH and the suspension is heated on a steam bath until a clear solution is formed. The 3-N-isoindolinyl-4-phenoxy-5-sulphamylbenzoic acid is precipitated with 2 N HCl and is recrystallised from glacial acetic acid.

Light yellow crystals, melting point 259° - 261°, with decomposition.

NMR data: (D$_6$-DMSO, 60 MHz, TMS) δ = 4.68 (s; 4H), δ = 6.6–8.0 (m; 13H) in ppm.

EXAMPLE 12

3-N-(2,4-Dioxo-3-azabicyclo-[3.2.0]-heptano)-4-phenoxy-5-sulphamylbenzoic acid methyl ester 8.1 g of 3-amino-4-phenoxy-5-sulphamylbenzoic acid methyl ester are mixed with 6.3 g of cis-cyclobutane-1,2-dicarboxylic acid anhydride and 5 ml of diglyme and the mixture is heated to 180°. In the course thereof the diglyme evaporates off. The melt becomes solid after about 1 hour. Methanol is added while it is still warm. The solid mass disintegrates into a colourless mash of crystals. The crystalline powder is filtered off and recrystallised from glycol monomethyl ether.

Melting point: 284° - 285° C.

EXAMPLE 13

3-N-(3-Azabicyclo-[3.2.0]-heptano)-4-phenoxy-5-sulphamylbenzoic acid methyl ester 7.3 g of 3-N-(2,4-dioxo-3-azabicyclo-[3.2.0]-heptano)-4-phenoxy-5-sulphamylbenzoic acid methyl ester are suspended in 70 ml of diglyme and 6 ml of boron trifluoride etherate are added. A solution of 1.5 g of NaBH$_4$ in 70 ml of diglyme is then added slowly dropwise, with ice cooling. The mixture is stirred for about 15 minutes more and the 3-N-(3-azabicyclo-[3.2.0]-heptano)-4-phenoxy-5-sulphamylbenzoic acid methyl ester is precipitated by adding water.

Recrystallisation is carried out from methanol or acetonitrile.

White crystals, melting point 176° - 177° C.

EXAMPLE 14

3-N-(3-Azabicyclo-[3.2.0]-heptano)-4-phenoxy-5-sulphamylbenzoic acid 6.2 g of 3-N-(3-azabicyclo-[3.2.0]-heptano)-4-phenoxy-5-sulphamylbenzoic acid methyl ester are suspended in 60 ml of 1 N NaOH and the suspension is heated on the waterbath until a clear solution is formed. The acid is then precipitated with 2 N HCl, while stirring well, and is recrystallised from glacial acetic acid.

Pale yellow platelets, melting point 254° - 255° C, with decomposition.

EXAMPLE 15

3-N-(cis-1,2-Cyclohexanedicarboximido)-4-phenoxy-5-sulphamylbenzoic acid methyl ester 8 g of 3-amino-4-phenoxy-5-sulphamylbenzoic acid methyl ester are fused with 7.5 g of cis-cyclohexane-1,2-dicarboxylic acid anhydride, with the addition of a few drops of diglyme. The temperature is kept at 180° - 200° C, while stirring, until the mass begins to solidify. Methanol is then added cautiously and the colourless substance which has crystallised out is filtered off.

Recrystallisation from glycol monomethyl ether gives white crystals, melting point 268° - 269° C.

EXAMPLE 16

3-N-(3,5-Dioxo-morpholino)-4-phenoxy-5-sulphamylbenzoic acid methyl ester 16 g of 3-amino-4-phenoxy-5-sulphamylbenzoic acid methyl ester are mixed with 15 g of diglycollic acid anhydride and 10 ml of diglyme and the mixture is heated in an open flask to about 180° C. After 1 - 2 hours, methanol is added cautiously. The imide crystallises out on cooling.

White crystals from diglyme; melting point 295° - 297° C.

EXAMPLE 17

3-N-Morpholino-4-phenoxy-5-sulphamylbenzoic acid methyl ester 9.4 g of 3-N-(3,5-dioxo-morpholino)-4-phenoxy-5-sulphamylbenzoic acid methyl ester are suspended in 100 ml of diglyme and 6 ml of boron trifluoride etherate are added. A solution of 1.9 g of NaBH$_4$ in 100 ml of diglyme is then added slowly dropwise, while cooling with ice and stirring well. The resulting 3-N-morpholino-4-phenoxy-5-sulphamylbenzoic acid methyl ester is precipitated by adding water.

Recrystallised from methanol; melting point 221° - 222° C.

EXAMPLE 18

3-N-Morpholino-4-phenoxy-5-sulphamylbenzoic acid

The corresponding methyl ester (Example 17) is heated with 1 N NaOH on the waterbath until a clear solution is formed. The 3-N-morpholino-4-phenoxy-5-sulphamylbenzoic acid is precipitated by adding 2 N HCl and is then recrystallised from methanol; brownish white crystals, melting point 194° - 197°, with decomposition.

EXAMPLE 19

3-N-(4-Methylglutarimido)-4-phenoxy-5-sulphamylbenzoic acid methyl ester 16 g of 3-amino-4-phenoxy-5-sulphamylbenzoic acid methyl ester and 15 g of 4-methylglutaric anhydride are mixed, with the addition of a little diglyme, to form a slurry which is heated to 160° – 180° C for 2 – 3 hours. The 3-N-(4-methylglutarimido)-4-phenoxy-5-sulphamylbenzoic acid methyl ester is precipitated by adding methanol; white crystals from glycol monomethyl ether; melting point 315° C.

EXAMPLE 20

3-N-(4-Methylpiperidino)-4-phenoxy-5-sulphamylbenzoic acid methyl ester 10.3 g of 3-N-(4-methylglutarimido)-4-phenoxy-5-sulphamylbenzoic acid methyl ester are suspended in 100 ml of diglyme and 6.5 ml of $BF_3$ etherate are added. A solution of 1.9 g of $NaBH_4$ in 100 ml of diglyme is added dropwise at room temperature. After the dropwise addition, the mixture is stirred for a further 15 minutes and the 3-N-(4-methylpiperidino)-4-phenoxy-5-sulphamylbenzoic acid methyl ester is then precipitated with water; colourless crystals from methanol, melting point 143° – 144° C.

EXAMPLE 21

3-N-(4-Methylpiperidino)-4-phenoxy-5-sulphamylbenzoic acid

The corresponding methyl ester (Example 20) is heated with 1 N NaOH on a waterbath until a clear solution is formed. The 3-N-(4-methylpiperidino)-4-phenoxy-5-sulphamylbenzoic acid is precipitated by adding 2 N HCl; white crystals from methanol/water, melting point 243° – 244° C.

EXAMPLE 22

3-N-(3-Methylsuccinimido)-4-phenoxy-5-sulphamylbenzoic acid methyl ester 16 g of 3-amino-4-phenoxy-5-sulphamylbenzoic acid methyl ester and 15 g of 3-methylsuccinic anhydride are fused together with a little diglyme in an open flask and the mixture is kept at approx. 180° C for about 2.5 hours. The 3-N-(3-methylsuccinimido)-4-phenoxy-5-sulphamylbenzoic acid methyl ester crystallises out on adding methanol.

Recrystallised from glycol monomethyl ether; white crystals, melting point 272° C.

EXAMPLE 23

3-N-(3-Methylpyrrolidino)-4-phenoxy-5-sulphamylbenzoic acid methyl ester 17 g of 3-N-(3-methylsuccinimido)-4-phenoxy-5-sulphamylbenzoic acid methyl ester are suspended in 150 ml of diglyme. 11 ml of $BF_3$ etherate are added and a solution of 3 g of $NaBH_4$ in 150 ml of diglyme is then added dropwise while cooling with ice. After the dropwise addition, the resulting 3-N-(3-methylpyrrolidino)-4-phenoxy-5-sulphamylbenzoic acid methyl ester is precipitated with water; white crystals from methanol, melting point 145° C.

EXAMPLE 24

3-N-(3-Methylpyrrolidino)-4-phenoxy-5-sulphamylbenzoic acid 9 g of 3-N-(3-methylpyrrolidino)-4-phenoxy-5-sulphamylbenzoic acid methyl ester are heated in 1 N NaOH on a waterbath until a clear solution is formed. The 3-N-(3-methylpyrrolidino)-4-phenoxy-5-sulphamylbenzoic acid is then precipitated at room temperature with 2 N HCl and is recrystallised from $CH_3OH/H_2O$; white-yellow crystals, melting point 206° – 208° C.

EXAMPLE 25

3-N-Maleimido-4-phenoxy-5-sulphamylbenzoic acid methyl ester 16 g of 3-amino-4-phenoxy-5-sulphamylbenzoic acid methyl ester and 15 g of maleic anhydride, together with a little diglyme, are heated in an open flask to about 180° C. After 3 hours the mixture is allowed to cool and methanol and a little water are added. The 3-N-maleimidio-4-phenoxy-5-sulphamylbenzoic acid methyl ester precipitates on standing for a prolonged period.

Recrystallised from methanol; white crystals, melting point 197° – 198° C.

EXAMPLE 26

3-N-Pyrrolidino-4-phenoxy-5-sulphamylbenzoic acid methyl ester    Method B 4.1 g of 3-N-succinimido-4-phenoxy-5-sulphamylbenzoic acid methyl ester are dissolved in 40 ml of diglyme and 2.5 ml of titanium tetrachloride are added. A solution of 1.1 g of $NaBH_4$ in 30 ml of diglyme is then added dropwise slowly at room temperature and the mixture is stirred for about 1 hour more.

The resulting 3-N-pyrrolidino-4-phenoxy-5-sulphamylbenzoic acid methyl ester is precipitated with water and recrystallised from methanol. Melting point 191° C.

EXAMPLE 27

3-N-(ω-Chloro-butyrylamino)-4-phenoxy-5-sulphamylbenzoic acid methyl ester 24 g of 3-amino-4-phenoxy-5-sulphamylbenzoic acid methyl ester and 7.5 ml of pyridine in 100 ml of absolute dioxane and 21.2 g of ω-chlorobutyric acid chloride in 100 ml of absolute acetone are added dropwise, slowly and as nearly as possible at the same rate, over the course of about 2 hours into a vessel containing 100 ml of boiling absolute dioxane. The solution is stirred for 1 hour more and is then concentrated. The residual oil is taken up in a little acetone and added dropwise, with vigorous stirring, to ice water.

The 3-N-(ω-chloro-butyrylamino)-4-phenoxy-5-sulphamyl-benzoic acid methyl ester is precipitated and is recrystallised from methanol. Melting point 151°–153° C.

EXAMPLE 28

3-N-(ω-chlorobutylamino)-4-phenoxy-5-sulphamylbenzoic acid methyl ester 12 g of 3-N-(ω-chlorobutyrylamino)-4-phenoxy-5-sulphamyl-benzoic acid methyl ester are suspended in 150 ml of diglyme. 7 ml of boron trifluoride etherate are added. A solution of 2.2 g of $NaBH_4$ in 150 ml of diglyme is slowly added dropwise at room temperature. Stirring is continued for some minutes and the product is then carefully precipitated with water. Recrystallisation from CH₃OH, m.p. 125° C.

EXAMPLE 29

3-N-pyrrolidino-4-phenoxy-sulphamyl-benzoic acid

Method C

3-N-(ω-chlorobutylamino)-4-phenoxy-5-sulphamyl-benzoic acid methyl ester is suspended in 1N NaOH and heated on a steam bath until a clear solution is obtained. 3-N-pyrrolidino-4-phenoxy-5-sulphamyl-benzoic acid (as in Example 5) is precipitated from the cold solution by means of 1N HCl.

EXAMPLE 30

4-Chloro-3-succinimido-5-sulphamyl-benzoic acid methyl ester 25.4 g of 4-chloro-3-amino-5-sulphamyl-benzoic acid methyl ester, m.p. 195°–196° C, are thoroughly mixed with 25 g of succinic acid anhydride and melted for 6 hours at 180° C. The melt is allowed to cool slowly and CH₃OH is added carefully. The product crystallizes. A small amount of water added completes the crystallisation.

Recrystalisation from glycol monomethyl ether: m.p. 267°–269° C.

EXAMPLE 31

4-Chloro-3-pyrrolidino-5-sulphamyl-benzoic acid 20 g of imide (Example 30) are suspended in 200 ml of diglyme and 17 ml of BF₃ etherate are added. A solution of 4 g of NaBH₄ in 200 ml of diglyme is added dropwise to this suspension while cooling with ice. After the addition, stirring is continued for half an hour and the mixture is then carefully hydrolysed with a small amount of water. The solution is filtered, and 4-chloro-3-pyrrolidino-5-sulphamyl-benzoic acid methyl ester is precipitated with water. Recrystallisation from methanol: m.p. 189°–191° C. The ester is saponified in 1N NaOH on a steam bath until a clear solution has formed. Upon acidification at pH 4, the free acid precipitates.

Light yellow crystals are obtained from CH₃OH/H₂O. M.p. 259°–261° C.

EXAMPLE 32

3-N-succinimido-4-phenylthio-5-sulphamyl-benzoic acid methyl ester 5.8 g of 3-amino-4-phenylthio-5-sulphamyl-benzoic acid methyl ester are mixed with 5.9 g of succinic acid anhydride and melted down at 170° C. After 5 hours, CH₃OH is carefully added while cooling. The substance crystallizes and is recrystallised from glycol monomethyl ether. M.p. 250°–251° C.

EXAMPLE 33

3-N-pyrrolidino-4-phenylthio-5-sulphamyl-benzoic acid 14.7 g of imide (Example 32) are suspended in 100 ml of diglyme and 10 ml of BF₃ etherate are added. 2.8 g of NaBH₄ dissolved in 100 ml of diglyme are then slowly added dropwise while cooling with ice. Stirring is continued for half an hour at room temperature and excess reducing agent is destroyed by adding a small amount of water. 3-N-pyrrolidino-4-phenylthio-5-sulphamyl-benzoic acid methyl ester is then precipitated with water and recrystallised from methanol. Yellow crystals having a melting point of 139°–140° C are obtained. The ester is heated with 1N NaOH on a steam bath until a clear solution is obtained, and the acid formed is then precipitated with 1N hydrochloric acid at pH 3 – 4. Upon recrystallisation from methanol/water, yellow crystals are obtained, m.p. 238°–239° C.

EXAMPLE 34

3-(1-Pyrrolidinyl)-4-phenoxy-5-sulphamylbenzoic acid

Method D (a) 3-N-succinimido-4-phenoxy-5-nitro-benzoic acid methyl ester 105 g of 3-amino-4-phenoxy-5-nitrobenzoic acid methyl ester are mixed with 210 g of succinic acid anhydride and heated for 2 hours to 180° C while stirring; the reaction mixture is introduced, with stirring, into 3 l of water and extracted after some time with methylene chloride. The organic phase is isolated, dried and concentrated. The residue yields, after recrystallization from methanol, the desired compound melting at 152°–154° C in a very good yield.

(b) 3-(1-Pyrrolidinyl)-4-phenoxy-5-nitrobenzoic acid methyl ester.

A solution of 44.4 g of the ester obtained according to (a) in 300 ml of diglyme under nitrogen is reacted, while stirring, at 0° C, with 34 g of boron trifluoro-dietherate and subsequently with a solution of 9.2 g of NaBH₄ in 200 ml of diglyme, while keeping the temperature below +15° C. After a further hour, water is added dropwise. After completion of the exothermic reaction, 500 ml of water are added. The desired compound thereupon separates in the form of orange coloured needles melting at 118°–120° C with a very good yield.

(c) 3-(1-Pyrrolidinyl)-4-phenoxy-5-amino-benzoic acid methyl ester.

A solution of 30 g of the nitrobenzoic acid methyl ester obtained according to (b) in 500 ml of dioxane is hydrogenated catalytically in the presence of Raney nickel. After completion of the absorption of hydrogen, the whole is filtered and the filtrate is concentrated. The residue yields, on recrystallization from methanol, the desired compound in the form of colourless crystals melting at 153°–156° C in a very good yield.

(d) 3-(1-Pyrrolidinyl)-4-phenoxy-5-chlorosulphonyl-benzoic acid methyl ester.

A solution of 24.3 g of the amino ester obtained according to c) in 150 ml of concentrated hydrochloric acid is cooled to −5° C and diazotized with a solution of 5.46 g of NaNO₂ in 40 ml of water, while keeping the temperature below +5° C. After 15 minutes, the light brown solution of the diazonium salt is introduced into a mixture of 7.8 g of Cu$^{II}$-chloride dihydrate, 24 ml of concentrated hydrochloric acid and 200 ml of a saturated solution of SO₂ in glacial acetic acid at 0° C. After completion of the evolution of gas, the whole is stirred for a short time, the reaction mixture is then combined with water and the sulphochloride that has separated is extracted with methylene chloride. The organic phase is washed twice with water, dried and concentrated. The remaining oil yields, upon addition of diisopropyl ether, the desired compound melting at 108°–112° C with a very good yield.

(e) 3-(1-Pyrrolidinyl)-4-phenoxy-5-sulphamyl-benzoic acid methyl ester.

25.0 g of the 5-chlorosulphonyl-benzoic acid methyl ester are introduced portionwise, while stirring, at room temperatures into a mixture of 150 ml of methylene chloride and 75 ml of 25% aqueous ammonia, the mixture is stirred for 1 hour, the organic phase is separated and washed with water, dried over sodium sulfate and concentrated. The remaining oil is recrystallised from methanol and gives the 5-sulphamylbenzoic acid ester melting at 186°–188° C with a very good yield.

Saponification of the ester to form the 3-(1-pyrrolidinyl)-4-phenoxy-5-sulphamylbenzoic acid is effected in the manner described in Example 5. Melting point: 227°–228° C.

EXAMPLE 35

3-(1-Pyrrolidinyl)-4-phenoxy-5-sulphamylbenzoic acid Method E (a) 3-(1-Pyrrolidinyl)-4-phenoxy-5-nitrobenzoic acid.

50 g of 3-(1-pyrrolidinyl)-4-phenoxy-5-nitrobenzoic acid methyl ester (preparation cf. Example 34, step (b) are saponified under heating with dilute sodium hydroxide solution.

The orange red solution is extracted twice with $CH_2Cl_2$, the aqueous phase is then acidified with concentrated hydrochloric acid. The desired acid is isolated in the form of light yellow crystals melting at 228°–230° C.

(b) 3-(1-Pyrrolidinyl)-4-phenoxy-5-aminobenzoic acid.

32.8 g of the nitrobenzoic acid prepared according to (a) are dissolved in a solution of 8 g of NaOH in 200 ml of water, cooled to 0° C and combined with a solution of 90 g of sodium dithionite in 380 ml of water, while keeping the temperature below 10° C. The solution which at first is red-orange coloured changes to light yellow. The solution is stirred for 1 hour without cooling, then acidified to pH 1 by means of concentrated hydrochloric acid and concentrated until crystallisation begins. The hydrochloride of the desired aminobenzoic acid is obtained in the form of colourless crystals melting at 245°–247° C.

If the dithionite contains sulfate, there is obtained already before concentration of the aqueous solution the corresponding sulphate in the form of colourless crystals melting at 175°–176° C.

From both, the free amine melting at 100°–103° C can be obtained by neutralisation of the aqueous solution to pH 4–4.5.

(c)
3-(1-Pyrrolidinyl)-4-phenoxy-5-chlorosulphonyl-benzoic acid.

A solution of 8.35 g of the aminobenzoic acid hydrochloride prepared according to (b) in 25 ml of concentrated hydrochloric acid is diazotized at 0° C with a solution of 1.75 g of sodium nitrite in 15 ml of water, while keeping the temperature below +5° C. After 15 minutes, the solution of the diszonium salt is introduced, while stirring, into a mixture cooled to 0° C of 2 g of Cu-dichloride-dihydrate, 2 ml of concentrated hydrochloric acid and 15 ml of a saturated soluion of $SO_2$ in glacial acetic acid. After termination of the foam formation, the whole is s stirred for 30 minutes, the reaction mixture is subsequently combined with 150 ml of water and extracted several times with ethyl acetate. The organic phase is washed with water, dried, concentrated and, after addition of ether and hexane, yields the crystalline sulphochloride melting at 163°–165° C.

If the aminobenzoic acid sulphate is used, the same sulphochloride is obtained with a somewhat smaller yield.

(d) 3-(1-Pyrrolidinyl)-4-phenoxy-5-sulphamylbenzoic acid.

7.6 g of the chlorosulphonyl derivative prepared according to (c) are introduced in 15 ml of liquid ammonia. The ammonia is removed by evaporation at room temperature and the residue is dissolved in a small amount of water. The solution is filtered and adjusted to pH 1 by means of concentrated hydrochloric acid. The desired sulphamylbenzoic acid is thereupon obtained in the form of brownish crystals which, upon recrystallisation from methanol/water, yield pale yellow crystals melting at 225° C.

EXAMPLE 36

4-Phenoxy-3-(1-pyrrolidinyl)-5-dimethylsulphamoyl-benzoic acid 7.2 g (0.02 mol) of 4-phenoxy-3-(1-pyrrolidinyl)-5-sulphamoylbenzoic acid are dissolved in 100 ml of 1 N NaOH and combined with 10 ml of dimethylsulphate. The mixture is well stirred at room temperature. After about 30 minutes, a white flocky substance precipitates. It is filtered off with suction and heated with 2 N NaOH on the steam bath. When a clear solution is formed, the whole is allowed to cool and the 4-phenoxy-3-(1-pyrrolidinyl)-5-dimethylsulphamoylbenzoic acid is precipitated with the aid of 2 N HCl. The substance can be recrystallized from methanol/water. Yellow fibers melting at 214°–215° C are obtained.

EXAMPLE 37

4-Phenoxy-3-(1-pyrrolidinyl)-5-methylsulphamoylbenzoic acid (a)
4-Phenoxy-3-N-succinimido-5-methylsulphamoylbenzoic acid methyl ester.

71 g of 3-amino-4-phenoxy-5-methyl-sulphamoylbenzoic acid methyl ester (M.p. 188° C) are fused with 87 g of succinic acid anhydride at 180°–190° C. After 5 hours, the molten mass is cautiously combined with methanol and thereafter with the same amount of water, whereupon the imide crystallises. The 4-phenoxy-3-N-succinimido-5-methylsulphamoylbenzoic acid methyl ester is obtained from methanol and is found to melt at 249°–250° C.

(b)
4-Phenoxy-3-(1-pyrrolidinyl)-5-methylsulphamoylbenzoic acid methyl ester.

67 g of 4-phenoxy-3-N-succinimido-5-methylsulphamoylbenzoic acid methyl ester are suspended in 300 ml of absolute diglyme and combined with 40 ml of boron trifluoride etherate. The mixture is cooled to −10° C and a solution of 12.2 g of $NaBH_4$ in 300 ml of diglyme is added dropwise, while well stirring. The temperature should during that time not rise above 10° C. After the dropwise addition, the whole is stirred for 10 minutes and then the mixture is cautiously combined with water (foaming). Upon further addition of water, the reaction product precipitates. The 4-phenoxy-3-(1-pyrrolidinyl)-5-methylsulphamoylbenzoic acid methyl ester melting at 138°–139° C is obtained by recrystallisation from methanol.

(c)

4-Phenoxy-3-(1-pyrrolidinyl)-5-methylsulphamoylbenzoic acid.

54 g of the methyl ester obtained according to b) are suspended in 50 ml of 1 N NaOH and heated, while stirring, on the steam bath. When a clear solution has formed, the whole is allowed to cool and the free acid is precipitated with the aid of 1 N-HCl. The 4-phenoxy-3-(1-pyrrolidinyl)-5-methylsulphamoylbenzoic acid melting at 245°–248° C with decomposition is obtained by recrystallisation from methanol/water.

EXAMPLE 38

4-(4'-Methylphenoxy)-3-(1-pyrrolidinyl)-5-sulphamoylbenzoic acid (a) 3-Nitro-4-(4'-methylphenoxy)-5-sulphamoylbenzoic acid.

124 g (0.9 mol) of potassium carbonate are dissolved in 800 ml of water. To this solution, there are added portionwise 1.6 mols of p-cresol and subsequently 112 g (0.4 mol) of 2-chloro-3-nitro-5-carboxy-benzenesulphonamide and the solution is heated to 85° C. The whole is stirred for 16 hours at this temperature, cooled to 25°–30° C and acidified with concentrated hydrochloric acid to pH 1. The oil which thereupon separates is isolated from the aqueous phase and subjected to steam distillation. Alternatively, it is also possible to adjust a pH-value of 8–9, to extract the excess phenol with ethyl acetate and then to acidify the aqueous phase. After having separated in this manner the excess p-cresol, the product crystallises upon cooling. By recrystallisation from acetone/H$_2$O, the 3-nitro-4-(4'-methylphenoxy)-5-sulphamoylbenzoic acid melting at 236° C is obtained.

(b) 3-Nitro-4-(4'-methylphenoxy)-5-sulphamoylbenzoic acid methyl ester.

The raw product obtained according to Example 38 (a) is dissolved in methanol and heated to the boiling temperature. Then, 5–10% of concentrated sulfuric acid (in relation to the benzoic acid used) are added and the whole is boiled for 8 hours under reflux. The solution is concentrated to one third and cooled to 5°–10° C. The methyl ester crystallises out: crystals melting at 161°–162° C.

(c)

3-Amino-4-(4'-methylphenoxy)-5-sulphamoylbenzoic acid methyl ester.

45 g of 3-nitro-4-(4'-methylphenoxy)-5-sulphamoylbenzoic acid methyl ester are suspended in 150 ml of ethyl acetate and hydrogenated for 5 hours with Raney nickel at 50° C and a hydrogen pressure of 100 atmospheres gauge. After cooling, the Raney nickel is separated and the solution is concentrated to dryness. The 3-amino-4-(4'-methylphenoxy)-4-sulphamoylbenzoic acid methyl ester is recrystallised from methanol/H$_2$O. Crystals melting at 183°–185° C.

(d)

3-N-Succinimido-4-(4'-methylphenoxy)-5-sulphamoylbenzoic acid methyl ester.

27 g (~ 0.08 mol) of 3-amino-4-(4'-methylphenoxy)-5-sulphamoylbenzoic acid methyl ester are fused with 24 g (~ 0.24 mol) of succinic acid anhydride for 4 hours at 170°–190° C. During cooling of the molten mass, methanol and a small amount of water are added with precaution. The imide precipitates and is recrystallised from CH$_3$OH/H$_2$O. Crystals melting at 240°–241° C.

(e)

4-(4'-Methylphenoxy)-3-(1-pyrrolidinyl)-5-sulphamoylbenzoic acid methyl ester.

25.6 g of 3-N-succinimido-4-(4'-methylphenoxy)-5-sulphamoylbenzoic acid methyl ester are suspended in 150 ml of absolute diglyme and 16 ml of BF$_3$-etherate are added. Then, a solution of 4.6 g of NaBH$_4$ in 200 ml of absolute diglyme is added dropwise and slowly, while cooling with ice and well stirring. The temperature should during that time not rise above 20° C. Stirring is continued for 15 minutes and eventually the product is precipitated with water. Recrystallisation from CH$_3$OH; crystals melting at 156°–157° C.

(f) The methyl ester obtained according to (e) os suspended in 1 N NaOH and heated on the steam bath until a clear solution has formed. The whole is filtered and acidified to pH 3. The 4-(4'-methylphenoxy)-3-(1-pyrrolidinyl)-5-sulphamoylbenzoic acid that has precipitated is recrystallised from methanol; light yellow crystals melting at 230°–233° C with decomposition.

EXAMPLE 39

4-(4'-Methoxyphenoxy)-3-(1-pyrrolidinyl)-5-sulphamoylbenzoic acid (a)

3-Nitro-4-(4'-methoxyphenoxy)-5-sulphamoylbenzoic acid.

The reaction is carried out with p-methoxyphenol in a manner analogous to that described in Example 38 a). The product is recrystallised from acetone/water and has a melting point of 233°–234° C.

(b)

3-Nitro-4-(4'-methoxyphenoxy)-5-sulphamoylbenzoic acid methyl ester.

In a manner analogous to that described in Example 38 (b). Recrystallisation from methanol; M.p. 150°–152° C.

(c)

3-Amino-4-(4'-methoxyphenoxy)-5-sulphamoylbenzoic acid methyl ester.

In a manner analogous to that described in Example 38 (c). Recrystallisation from methanol; M.p. 176°–177° C.

(d)

3-N-succinimido-4-(4'-methoxyphenoxy)-5-sulphamoylbenzoic acid methyl ester.

In a manner analogous to that described in Example 38 (d). M.p. 226°–227° C.

(e)
4-(4'-Methoxyphenoxy)-3-(1-pyrrolidinyl)-5-sulphamoylbenoic acid methyl ester.

In a manner analogous to that described in Example 38 (e). M.p. 190°-191° C.

(f) The 4-(4'-methoxyphenoxy)-3-(1-pyrrolidinyl)-5-sulphamoylbenzoic acid is prepared in a manner analogous to that described in Example 38 (f) and recrystallised from methanol/water. Light yellow crystals melting at 228°-229° C.

EXAMPLE 40

4-(3',5'-Dimethylphenoxy)-3-(1-pyrrolidinyl)-5-sulphamoylbenzoic acid (a)
3-Nitro-4-(3',5'-dimethylphenoxy)-5-sulphamoylbenzoic acid.

The reaction is carried out with 3,5-dimethylphenol in a manner analogous to that described in Example 38 (a). The raw product so obtained is directly esterified.

(b)
3-Nitro-4-(3',5'-dimethylphenoxy)-5-sulphamoylbenzoic acid methyl ester.

In a manner analogous to that described under Example 38 (b), recrystallisation from methanol. M.p. 197°-198° C.

(c)
3-Amino-4-(3',5'-dimethylphenoxy)-5-sulphamoylbenzoic acid methyl ester.

In a manner analogous to that described under Example 38 (c), recrystallisation from methanol. M.p. 195°-196° C.

(d)
3-N-Succinimido-4-(3',5'-dimethylphenoxy)-5-sulphamoylbenzoic acid methyl ester.

In a manner analogous to that described under Example 38 (d), recrystallisation from methanol. M.p. sintering from 220° C onwards.

(e)
4-(3',5'-Dimethylphenoxy)-3-(1-pyrrolidinyl)-5-sulphamoylbenzoic acid methyl ester.

In a manner analogous to that described under Example 38 (e), recrystallisation from methanol. M.p. 208°-209° C.

(f) In a manner analogous to that described in Example 38 (f). The 4-(3',5'-dimethylphenoxy)-3-(1-pyrrolidinyl)-5-sulphamoylbenzoic acid is recrystallised from methanol/water; M.p. 246°-248° C with decomposition.

EXAMPLE 41

4-(4'-Chlorophenoxy)-3-(1-pyrrolidinyl)-5-sulphamoylbenzoic acid (a) 3-Nitro-4-(4'-chlorophenoxy)-5-sulphamoylbenzoic acid.

Preparation with p-chlorophenol in a manner analogous to that described in Example 38 (a). Recrystallisation from acetone/ water; M.p. 248° C.

(b) 3-Nitro-4-(4'-chlorophenoxy)-5-sulphamoylbenzoic acid methyl ester.

In a manner analogous to that described in Example 38(b); recrystallisation from methanol; M.p. 171°-172° C.

(c)
3-Amino-4-(4'-chlorophenoxy)-5-sulphamoylbenzoic acid methyl ester.

In a manner analogous to that described in Example 38 c); recrystallisation from methanol; M.p. 198°-199° C.

(d)
3-N-Succinimido-4-(4'-chlorophenoxy)-5-sulphamoylbenzoic acid methyl ester.

In a manner analogous to that described in Example 38(d); recrystallisation from methanol; M.p. 266°-267° C.

(e)
4-(4'-Chlorophenoxy)-3-(1-pyrrolidinyl)-5-sulphamoylbenzoic acid methyl ester.

In a manner analogous to that described in Example 38 e); recrystallisation from methanol/water; M.p. 200° C.

(f)
4-(4'-Chlorophenoxy)-3-(1-pyrrolidinyl)-5-sulphamoylbenzoic acid.

In a manner analogous to that described in Example 38(f); recrystallisation from methanol; M.p. 253°-254° C.

EXAMPLE 42

4-(3'-Trifluoromethylphenoxy)-3-(1-pyrrolidinyl)-5-sulphamoylbenzoic acid (a)
3-Nitro-4-(3'-trifluoromethylphenoxy)-5-sulphamoylbenzoic acid.

In a manner analogous to that described in Example 38(a) with 3-trifluoromethylphenol. Recrystallisation from acetone/water. M.p. 210° C.

(b)
3-Nitro-(3'-trifluoromethylphenoxy)-5-sulphamoylbenzoic acid methyl ester.

In a manner analogous to that described in Example 38(b); recrystallisation from methanol; M.p. 141°-143° C.

(c)
3-Amino-4-(3'-trifluoromethylphenoxy)-5-sulphamoylbenzoic acid methyl ester.

In a manner analogous to that described in Example 38(c); recrystallisation from methanol; M.p. 186°-187° C.

(d)
3-N-Succinimido-4-(3'-trifluoromethylphenoxy)-5-sulphamoylbenzoic acid methyl ester.

In a manner analogous to that described in Example 38(d); recrystallisation from methanol; M.p. 227°-228° C.

(e) 4-(3'-Trifluoromethylphenoxy)-3-(1-pyrrolidinyl)-5-sulphamoylbenzoic acid methyl ester.

In a manner analogous to that described in Example 38(e); recrystallisation from methanol; M.p. 170°-171° C.

(f) 4-(3'-Trifluoromethylphenoxy)-3-(1-pyrrolidinyl)-5-sulphamoylbenzoic acid.

In a manner analogous to that described in Example 38(f); recrystallisation from glacial acetic acid; M.p. 230°-234° C.

EXAMPLE 43

3-(1-Pyrrolidinyl)-4-phenoxy-5-sulphamoylbenzoic acid    Method F (a) 3,5-Dinitro-4-phenoxy-benzoic acid methyl ester.

30 g of 3,5-dinitro-4-phenoxy-benzoic acid in 200 ml of methanol are combined with 3 ml of concentrated sulphuric acid and the whole is boiled for 3 hours under reflux. After evaporation of the solvent, the residue is dissolved in ethyl acetate, and traces of unreacted acid are destroyed with dilute sodium bicarbonate solution. After drying of the ethyl acetate solution, the solvent is eliminated by evaporation, the residue is recrystallised from ethyl acetate/methanol. The desired ester melting at 171°-173° C is obtained with a very good yield.

(b) 3,5-Diamino-4-phenoxy-benzoic acid methyl ester.

25 g of 3,5-dinitro-4-phenoxy-benzoic acid methyl ester are dissolved in 250 ml of ethyl acetate, combined with 10 g of Raney nickel and hydrogenated. After absorption of the calculated amount of hydrogen, the catalyst is filtered off, the solvent is removed, whereupon the remaining oil crystallises. The raw product may be further reacted directly or recrystallized from methanol/water, whereby the diamino ester is obtained in form of colorless crystals melting at 140°-142° C in excellent yield. Alternatively, the hydrogenation may also be carried out in an autoclave at 50° C and 100 atmospheres gauge pressure. The reaction time is then 3 to 5 hours, depending on the reactivity of the Raney nickel.

(c) 3-Succinylamino-4-phenoxy-5-amino-benzoic acid methyl ester.

30 g of 3,5-diamino-4-phenoxy-benzoic acid methyl ester in 300 ml of chloroform or methylene chloride are stirred for 8 hours, at room temperature, with 12,8 g of succinic acid anhydride, whereupon the desired benzoic acid methyl ester separates in the form of a colourless precipitate. The crystals that have separated are isolated, washed with chloroform and recrystallised from methanol. The 3-succinylamino-4-phenoxy-5-aminobenzoic acid methyl ester melting at 190°-192° C is obtained in the form of colourless crystals.

(d) 3-(1-Succinimido)-4-phenoxy-5-amino-benzoic acid methyl ester.

30 g of 3-succinylamino-4-phenoxy-5-amino-benzoic acid methyl ester are introduced into a mixture of 260 ml of orthophosphoric acid and 60 g of $P_2O_5$, the whole is heated for 2 hours to 50° C, then cooled and introduced into 750 ml of water. The 3-(succinimido)-4-phenoxy-5-amino-benzoic acid methyl ester is isolated in the form of colourless crystals melting at 200° C-201° C with almost quantitative yield.

(e) 3-(1-Pyrrolidinyl)-4-phenoxy-5-aminobenzoic acid methyl ester.

A solution of 24 g of 3-(1-succinimido)-4-phenoxy-5-aminobenzoic acid methyl ester in 180 ml of diglyme is combined with 20 g of boron trifluoride-etherate and cooled to 10° C. A solution of 5.7 g of $NaBH_4$ in 125 ml de diglyme is added dropwise, while cooling, to the reaction mixture in such a manner that the temperature does not rise above 15° C. After completion of the addition, the reaction mixture is stirred for 1 hour and then decomposed cautiously with 300 ml of water. The solid substance that has precipitated is isolated and crystallized from methanol. The 3-(1-pyrrolidinyl)-4-phenoxy-5-amino-benzoic acid methyl ester melting at 154°-156° C is isolated with excellent yield.

(f) 3-(1-Pyrrolidinyl)-4-phenoxy-5-sulphamoylbenzoic acid.

The reaction order described in Example 34 is repeated. Over the 3-(1-pyrrolidinyl)-4-phenoxy-5-chlorosulphonyl-benzoic acid methyl ester, there is obtained by reaction with concentrated ammonia the desired 3-(1-pyrrolidinyl)-4-phenoxy-sulphamoylbenzoic acid methyl ester (M.p. 186°-138° C) which can be converted by heating with sodium hydroxide solution and subsequent acidification into the desired 3-(1-pyrrolidinyl)-4-phenoxy-5-sulphamylbenzoic acid melting at 226°-228° C.

EXAMPLE 44

3-(1-Pyrrolidinyl)-4-phenoxy-5-sulphamylbenzoic acid

The reaction order described in Example 43 is repeated until the 3-succinylamino-4-phenoxy-aminobenzoic acid. Then, 10 g of the 3-succinylamino-4-phenoxy-5-aminobenzoic acid ester are stirred for 2 hours at 200° C. After cooling, the reaction mixture is recrystallised from methanol and yields with good yield the 3-succinimido-4-phenoxy-5-amino-benzoic acid methyl ester; M.p. 199°-200° C.

The product so obtained is converted in the manner described in Example 43 into the desired 3-(1-pyrrolidinyl)-4-phenoxy-5-sulphamylbenzoic acid melting at 227°-228° C.

EXAMPLE 45

3-(1-Pyrrolidinyl)-4-phenoxy-4-sulphamylbenzoic acid

The reaction sequence described in Example 43 is repeated until step (e).

51 g of 3-(1-pyrrolidinyl)-4-phenoxy-5-amino-benzoic acid methyl ester in 780 ml of 1N sodium hydroxide solution are heated for 2 hours to the boil, whereupon a clear solution forms. The reaction mixture is subsequently cooled, adjusted to pH 4 and the product that has precipitated is dissolved in 60 ml of 2N HCl. After a short standing, the hydrochloride of 3-(1-pyrrolidinyl)-4-phenoxy-5-amino-benzoic acid melting at 245°-257° C crystallises in beautiful crystals. Mixed melting point with the product of Example 35 (step b): 252°-254° C.

The hydrochloride of the 3 -(1-pyrrolidinyl)-4-phenoxy-5-aminobenzoic acid is converted in the manner described in Example 35 over the 3-(1-pyrrolidinyl)-4-phenoxy-5-chlorosulphonyl-benzoic acid into the desired 3-(1-pyrrolidinyl)-4-phenoxy-5-sulphamylbenzoic acid melting at 225°-226° C.

EXAMPLE 46

4-(4'-Methylphenoxy)-3N-(3-methylpyrrolidinyl)-5-sulphamoylbenzoic acid (a)

3N-(3-Methylsuccinimido)-4-(4'-methylphenoxy)-5-sulphamoylbenzoic acid methyl ester.

20 g of 3-amino-4-(4'-methylphenoxy)-5-sulphamoylbenzoic acid methyl ester (cf. Example 38 c)) are fused with 18 g of methylsuccinic acid anhydride for 3 hours at 180° C. During cooling of the molten mass, the product crystallises on addition of methanol. It is recrystallised from acetone/water. M.p. 229°-230° C.

(b)

4-(4'-Methylphenoxy)-3N-(3-methylpyrrolidinyl)-5-sulphamoylbenzoic acid methyl ester.

22 g of 3N-(3-methylsuccinimido)-4-(4'-methyphenoxy)-5-sulphamoylbenzoic acid methyl ester methyl ester are suspended in 200 ml of absolute diglyme and combined with 13 ml of BF$_3$-etherate. A solution of 3.3 g of NaBH$_4$ in 200 ml of diglyme is then added dropwise and slowly, while well stirring, at -5°-0° C. Stirring is continued for 1 hour and the product that has formed is precipitated with water. Recrystallisation from methanol/water. M.p. 177°-178° C.

(c)

4-(4'-Methylphenoxy)-3N-(3-methylpyrrolidinyl)-5-sulpamoylbenzoic acid.

14 g of methyl ester (46 b)) are suspended in 150 ml of 1N-NaOH and heated on the stream bath, while well stirring. When a clear solution has formed, stirring is continued for 1 hour and the mixture is acidified with 2N-HCl to a pH of ∼3, while cooling with ice. The product that has precipitated is filtered off with suction, washed thoroughly with water and recrystallised from methanol/water. M.p. 220°-221° C.

EXAMPLE 47

4-Phenoxy-3-(1-pyrrolidinyl)-5-sulphamoylbenzoic acid   Method G (a)

4-Chloro-5-N,N-dimethylaminomethyleneaminosulphonylbenzoic acid.

90 ml (1.25 mol) of thionyl chloride are added dropwise, at −10° C, to a solution of 58.9 g (0.25 mol) of 4-chloro-5-sulphamoylbenzoic acid in 183 g (2.5 mols) of dimethylformamide (DMF). The solution is then allowed to reach room temperature, stirred for 2 hours and poured on ice, the precipitate is filtered off and washed with water until neutral. The 4-chloro-5-N,N-dimethylaminomethyleneamino-sulphonylbenzoic acid is obtained with very good yield in the form of crystals melting at 266°-267° C.

(b)

3-Nitro-4-chloro-5-N,N-dimethylaminomethyleneaminosulphonylbenzoic acid.

42 ml of fuming nitric acid are added dropwise, while cooling with ice, to 60 ml of 20% oleum, then 34.9 g (0.12 mol) of 4-chloro-5-N,N-dimethylaminomethyleneaminosulphonylbenzoic acid are introduced slowly. After having stirred for 24 hours at 55°-60° C, the solution is cooled to room temperature, poured onto ice and the precipitate is washed with water until neutral. 3-Nitro-4-chloro-5-N,N-dimethylaminomethyleneaminosulphonylbenzoic acid is obtained in the form of crystals melting at 274°-276° C.

(c)

3-Nitro-4-chloro-5-N,N-dimethylaminomethyleneaminosulphonylbenzoic acid methyl ester.

50.4 g (0.15 mol) of 3-nitro-4-chloro-5-N,N-dimethylaminomethylaneaminosulphonylbenzoic acid are boiled for 1 hour under reflux in a solution of 150 ml of thionyl chloride which contains 5 drops of DMF. After removal of the excess thionyl chloride under reduced pressure, the solid acid chloride is suspended in 200 ml of methanol. The suspension is boiled for one-half hour under reflux, then cooled, filtered and washed with cold methanol.

3-Nitro-4-chloro-5-N,N-dimethylaminomethyleneaminosulphonylbenzoic acid methyl ester is obtained in the form of crystals melting at 168°-169° C.

(d)

3-Nitro-4-phenoxy-5-N,N-dimethylaminomethyleneaminosulphonylbenzoic acid methyl ester.

A solution of 105 g (0.3 mol) of 3-nitro-4-chloro-5-N,N-dimethylaminomethyleneaminosulfphonyl-benzoic acid methyl ester and 47.5 g (0.36 mol) of potassium phenolate in 600 ml of DMF is boiled for 2 hours under reflux. After cooling and removal of the potassium chloride by filtration, the solution is poured onto ice/water and stirred for 1 hour. The precipitate is filtered off, washed with water and dried.

After dissolution of the raw product in 900 ml of acetone, the solution is clarified with charcoal, evaporated to 500 ml and diluted with 1 liter of methanol. After having stirred for 1 hour at 10° C, the precipitate is filtered off and washed with cold methanol.

3-Nitro-4-phenoxy-5-N,N-dimethylaminomethyleneaminosulphonyl-benzoic acid methyl ester is obtained in the form of crystals melting at 191°-193° C.

(e)

3-Amino-4-phenoxy-5-N,N-dimethylaminomethyleneaminosulphonylbenzoic acid methyl ester.

61 g (0.15 mol) of 3-nitro-4-phenoxy-5-N,N-dimethylaminomethyleneaminosulphonyl-benzoic acid methyl ester are hydrogenated with Raney nickel in methanol at room temperature and normal pressure for 8 hours. After filtration, the catalyst is suspended in warm DMF, filtered and the DMF filtrate is poured into a mixture of ice and water.

3-Amino-4-phenoxy-5-N,N-dimethylaminomethyleneaminosulphonylbenzoic acid methyl ester is obtained in the form of crystals melting at 255°-256° C.

(f)

3-N-Succinimido-4-phenoxy-5-N,N-dimethylaminomethyleneaminosulphonyl-benzoic acid methyl ester.

30 g of 3-amino-4-phenoxy-5-N,N-dimethylaminomethyleneaminosulphonyl-benzoic acid methyl ester are fused at 180° C with 25 g of succinic acid anhydride. After a reaction time of about 2 hours, the imide that has formed is precipitated with methanol. The imide melting at 283°-284° C is obtained with very good yield by recrystallisation from n-butanol.

(g)
4-Phenoxy-3-(1-pyrrolidinyl)-5-N,N-dimethylaminomethyleneaminosulphonyl-benzoic acid methyl ester.

23 g (0.05 mol) of 3-N-succinimido-4-phenoxy-5-N,N-dimethylaminomethyleneaminosulphonyl-benzoic acid methyl ester are suspended in 200 ml of diethylene glycol-dimethyl ether (diglyme) and 13 ml of $BF_3$-etherate (0.1 mol) are added. Then, a solution of 3.8 g (0.1 mol) of $NaBH_4$ in 200 ml of diglyme is added dropwise and slowly, while cooling and keeping the temperature in the range of from −10° to +5° C. The mixture is allowed to heat to room temperature, whereupon a clear solution is formed. The reaction is completed after 1.25 hour. The product precipitates by the addition of water. By recrystallisation from methanol, there is obtained the 4-phenoxy-3-(1-pyrrolidinyl)-5-N,N-dimethylaminomethyleneaminosulphonyl-benzoic acid ester melting at 189°-190° C.

(h) 4-Phenoxy-3-(1-pyrrolidinyl)-5-sulphamylbenzoic acid.

13 g (∼ 0.03 mol) of 4-phenoxy-3-(1-pyrrolidinyl)-5-N,N-dimethylaminomethyleneaminosulfphonyl-benzoic acid methyl ester are suspended in 100 ml of 2N-NaOH and saponified at 80°-90° C, while well stirring. When a clear solution has formed, stirring is continued for 1 hour at the same temperature. The solution is cooled to 0° C and 110 ml of 2N-hydrochloric acid are slowly added, while well stirring. The whole is stirred more intensively for one-half hour and the product that has precipitated in fine form is filtered off sharply with suction. The substance is recrystallized from methanol/water. Light yellow platelets melting at 226°-228° C.

EXAMPLE 48

The reaction sequence described in Example 47 is repeated until step (c). The 3-nitro-4-chloro-5-N,N-dimethylaminomethyleneaminosulphonyl-benzoic acid methyl ester is subsequently heated with potassium phenolate for 2 hours to 190°-200° C. The reaction mixture is cooled, dissolved in acetone and, after having removed inorganic components, worked up in the manner described in step (d). 3-Nitro-4-phenoxy-5-N,N-dimethylaminomethyleneaminosulphonylbenzoic acid methyl ester is obtained which can be converted in the manner described in Example 47 into the desired final product.

EXAMPLE 49

(a) The reaction sequence described in Example 47 is repeated with the difference that the catalytical hydrogenation of the 3-nitro-4-phenoxy-5-N,N-dimethylaminomethyleneaminosulphonyl-benzoic acid methyl ester is carried out in an autoclave at 50° C and 50 atmospheres gauge pressure. After cooling, the desired 3-amino-4-phenoxy-5-N,N-dimethylaminomethyleneaminosulphonylbenzoic acid ester is isolated in the manner described in Example 1(e).

(b) The reaction sequence described in Example 47 is repeated with the difference that the catalytical hydrogenation of the 3-nitro-4-phenoxy-5-N,N-dimethylaminomethyleneaminosulphonylbenzoic acid methyl ester is carried out in dimethylformamide (DMF) with Raney nickel at room temperature and normal pressure. After removal of the catalyst by filtration, the DMF solution is poured onto ice. 3-Amino-4-phenoxy-5-N,N-dimethylaminomethyleneamino-sulphonyl-benzoic acid methyl ester is obtained; M.p. 255°-256° C.

EXAMPLE 50

The reaction sequence described in Example 47 is repeated with the difference that 4-chloro-5-N,N-dimethylaminomethyleneamino-sulphonyl-benzoic acid methyl ester is used as starting compound.

(a) 4-Chloro-5-N,N-dimethylaminomethyleneaminosulphonylbenzoic acid methyl ester.

90 ml (1.25 mol) of thionyl chloride are added dropwise, at −10° C, to a solution of 74.9 g (0.3 mol) of 4-chloro-5-sulphamoylbenzoic acid methyl ester in 183 g (2.5 mols) of dimethylformamide and worked up as described in Example 47. 4-Chloro-5-N,N-dimethylaminomethyleneaminosulphonyl-benzoic acid methyl ester melting at 174°-176° C is obtained.

(b) 3-Nitro-4-chloro-5-N,N-dimethylaminomethyleneaminosulphonyl-benzoic acid methyl ester.

36.5 g (0.12 mol) of 4-chloro-5-N,N-dimethylaminomethyleneaminosulphonyl-benzoic acid methyl ester are reacted under the same conditions as those described in Example 47 b). A mixture of 3-nitro-4-chloro-5-N,N-dimethylaminomethyleneaminosulphonylbenzoic acid and 3-nitro-4-chloro-5-N,N-dimethylaminomethyleneaminosulphonyl-benzoic acid methyl ester is obtained. The mixture is separated by treatment with 5% aqueous sodium carbonate. 3-Nitro-4-chloro-5-N,N-dimethylaminomethyleneamino-sulphonylbenzoic acid methyl ester melting at 168°-169° C and after acidification 3-nitro-4-chloro-5-N,N-dimethylaminomethyleneaminosulphonylbenzoic acid melting at 270°-272° C are obtained; the latter can also be converted into the ester in the manner described in Example 47 c).

The further reaction is then effected according to the reaction sequence described in Example 47.

EXAMPLE 51

The nitration described in Example 47 is carried out with the difference that the ethyl ester is used instead of the methyl ester.

(a) 4-Chloro-5-N,N-dimethylaminomethyleneaminosulphonylbenzoic acid ethyl ester.

90 ml (1.25 mol) of thionyl chloride is added dropwise at −10° C to a solution of 65 g (0.25 mol) of 4-chloro-4-sulphamylbenzoic acid ethyl ester in 183 g (2.5 mols) of DMF and worked up as described in Example 1. 4-Chloro-5-N-N-dimethylaminomethyleneaminosulphonyl-benzoic acid ethyl ester is obtained in the form of crystals melting at 119°-121° C.

(b) 3-Nitro-4-chloro-5-N,N-dimethylaminomethyleneaminosulphonyl-benzoic acid ethyl ester.

38.3 g (0.12 mol) of 4-chloro-5-N,N-dimethylaminomethyleneaminosulphonyl-benzoic acid ethyl ester are reacted under the same conditions as those described in Example 50. Separation of the nitro-ester and of the nitro-acid is effected as described in Example 5. 3-Nitro-4-chloro-5-N,N-dimethylaminomethyleneaminosulphonyl-benzoic acid ethyl ester is obtained in the form of crystals melting at 182°–184° C, and, after acidification of the aqueous solution, the 3-nitro-4-chloro-5-N,N-dimethylaminomethyleneaminosulphonyl-benzoic acid is obtained in the form of crystals melting at 270°–272° C, which, according to melting point and mixture is identical with the carboxylic acid described in Example 1 (b).

EXAMPLE 52

3-Nitro-4-phenoxy-5-sulphamylbenzoic acid

The reaction sequence described in Example 47 is repeated until the stage of the 3-nitro-4-phenoxy-5-N,N-dimethylaminomethyleneaminosulfphonyl-benzoic acid ester. Then, 100 g of 3-nitro-4-phenoxy-5-N,N-dimethylaminomethyleneaminosulphonylbenzoic acid methyl ester are boiled for 2 hours under reflux in 500 ml of 2N-NaOH. After cooling, the mixture is acidified with concentrated hydrochloric acid. 3-Nitro-4-phenoxy-5-sulphamylbenzoic acid is obtained in the form of crystals melting at 254°–255° C.

EXAMPLE 53

4-Phenoxy-3-(1-pyrrolidinyl)-5-sulphamoyl-benzoic acid methyl ester 36.2 g of 4-phenoxy-3-(1-pyrrolidinyl)-5-sulphamoyl-benzoic acid are dissolved in 200 ml of methanol and 7 ml of concentrated $H_2SO_4$ and heated for 4 to 6 hours under reflux. Upon cooling, the ester crystallises. Recrystallisation from methanol; M.p. 191° C.

EXAMPLE 54

4-Phenylmercapto-3-(1-pyrrolidinyl)-5-sulphamoylbenzoic acid

The reaction sequence described in Example 47 for the preparation of 3-nitro-4-chloro-5-N,N-dimethylaminomethyleneaminosulphonylbenzoic acid methyl ester is repeated.

(a)
3-Nitro-4-phenylmercapto-5-N,N-dimethylaminomethyleneaminosulphonyl-benzoic acid methyl ester.

A solution of 21 g (0.06 mol) of 3-nitro-4-chloro-5-N,N-dimethylaminomethyleneaminosulphonylbenzoic acid methyl ester, 7.7 g (0.07 mol) of thiophenol and 8.2 g (0.077 mol) of sodium carbonate in 100 ml of DMF is boiled for 2 hours under reflux. After cooling and filtration, the solution is poured onto a mixture of ice and water and stirred for 1 hour. The precipitate is filtered off, washed with water and dried. The raw product is recrystallised from acetone/methanol. 3-Nitro-4-phenylmercapto-5-N,N-dimethylaminomethyleneaminosulphonylbenzoic acid methyl ester is obtained in the form of crystals melting at 207° C.

(b)
3-Amino-4-phenylmercapto-5-N,N-dimethylaminomethyleneaminosulphonylbenzoic acid methyl ester.

2 g (0.0047 mol) of 3-nitro-4-phenylmercapto-5-N,N-dimethylaminomethyleneaminosulphonylbenzoic acid methyl ester are hydrogenated for 8 hours with Raney nickel in 30 ml of DMF at room temperature and normal pressure. The catalyst is removed by filtration with suction, washed with warm DMF and the DMF filtrate is poured onto a mixture of ice and water.

3-Amino-4-phenylmercapto-5-N,N-dimethylaminomethyleneaminosulphonylbenzoic acid methyl ester is obtained from acetone in the form of crystals melting at 214°–215° C.

(c)
3-N-Succinimido-4-phenylmercapto-5-N,N-dimethylaminomethyleneaminosulphonyl-benzoic acid methyl ester.

35 g (0.089 mol) of 3-amino-4-phenylmercapto-5-dimethylaminomethyleneaminosulphonyl-benzoic acid methyl ester are finely triturated with 26.6 g (0.2668 mol) of succinic acid anhydride and fused for 2 hours at 175° C. After cooling to 150° C, the whole is diluted with 100 ml of DMF and the solution is poured slowly onto a mixture of ice and ater. The precipitate is filtered off with suction, dried and recrystallised from DMF/$CH_3OH$. M.p. 261°–263° C.

(d)
4-Phenylmercapto-3-(1-pyrrolidinyl)-5-N,N-dimethylaminomethyleneaminosulphonyl-benzoic acid methyl ester.

A solution of 5.1 g of $NaBH_4$ in 135 ml of absolute diglyme is added dropwise, at a temperature of 0°–10° C, while well stirring, to a solution of 32 g of 3-N-succinimido-4-phenylmercapto-5-N,N-dimethylaminomethyleneaminosulphonyl-benzoic acid methyl ester and 17.5 ml of $BF_3$-etherate in 135 ml of absolute diglyme. After 2 hours, the whole is hydrolysed and the product is precipitated by further addition of water.

(e) The raw product that has precipitated is heated under reflux with 2 N-NaOH until a clear solution is formed. The 4-phenylmercapto-3-(1-pyrrolidinyl)-5-sulphamoylbenzoic acid is precipitated with the aid of 2N-HCl and recrystallised from $CH_3OH/H_2O$. M.p. 237°–238° C (see also Example 33).

EXAMPLE 55

4-Phenylmercapto-3-[1-(3-methylpyrrolidinyl)]-5-sulphamoylbenzoic acid

(a)
3-Amino-4-phenylmercapto-5-N,N-dimethylaminomethyleneaminosulphonyl-benzoic acid methyl ester.

A solution of 110 g of 3-nitro-4-phenylmercapto-5-N,N-dimethylaminomethyleneaminosulphonylbenzoic acid methyl ester in 400 ml of DMF is hydrogenated for 8 hours over ~ 10 g of Raney nickel at 40° C and 100 atmospheres gauge pressure. The catalyst is filtered off and the solution is poured onto ice. The precipitate is filtered off, dried and recrystallised from acetone. M.p. 214°–215° C.

(b)
3N-(3-Methylsuccinimido)-4-phenylmercapto-5-N,Ndimethylaminomethyleneaminosulphonyl-benzoic acid methyl ester.

40 g (0.1 mol) of 3-amino-4-phenylmercapto-5-N,N-dimethylaminomethyleneaminosulphonyl-benzoic acid methyl ester are fused with 34 g (0.3 mol) of methylsuccinic acid anhydride for 2.5 hours at 175° C. After cooling to 150° C, the whole is diluted with 100 ml of DMF and the solution is poured slowly onto a mixture of ice and water. The precipitate is filtered off with suction and recrystallised from $CH_3OH$. M.p. 206°–207° C.

(c)
4-Phenylmercapto-3-[1-(3-methylpyrrolidinyl)]-5-N,N-dimethylaminomethyleneaminosulphonyl-benzoic acid methyl ester.

A solution of 4.65 g of NaBH$_4$ in 120 ml of absolute diglyme is added dropwise, at 0°–10° C, to a solution of 29.4 g of 3-N-(3-methylsuccinimido)-4-phenylmercapto-5-N,N-dimethylaminomethyleneaminosulphonyl-benzoic acid methyl ester and 15.9 ml of BF$_3$-etherate in 120 ml of absolute diglyme. After having stirred for 2 hours, the reaction product is precipitated cautiously with water. Recrystallisation from CH$_3$OH. M.p. 147°–148° C.

(d)
4-Phenylmercapto-3-[1-(3-methylpyrrolidinyl)]-5-sulphamoylbenzoic acid.

4 g of the ester (Example 55 c)) are heated for 2 hours under reflux in 40 ml of 2N-NaOH. A clear solution is formed. After cooling and acidification with 2N-HCl to pH 2-3, the 4-phenylmercapto-3-[1-(3-methylpyrrolidinyl)]-5-sulphamoyl-benzoic acid precipitates. It is recrystallised from CH$_3$OH/H$_2$O. Yellow crystals melting at 216°–217° C.

EXAMPLE 56

4-Phenoxy-3-(1-pyrrolidinyl)-5-sulphamoylbenzoic acid    Method H (a) 3-N-Pyrrolo-4-phenoxy-5-sulphamoylbenzoic acid.

8 g of 3-amino-4-phenoxy-5-sulphamoylbenzoic acid methyl ester are heated udner reflux with 5 g of 2,5-dimethoxytetrahydrofurane in 100 ml of glacial acetic acid. After 1.5 to 2 hours, the mixture is stirred into ice-water. The raw product which is thereby precipitated is heated on the steam bath with 1N-NaOH until a clear solution has formed. Upon acidification with 2N-HCl the 3-N-pyrrolo-4-phenoxy-5-sulphamoylbenzoic acid precipitates. It can be recrystallised from methanol or glacial acetic acid/water. White grey crystals melting at 214° C.

(b) 8.8 g of 3-N-pyrrolo-4-phenoxy-5-sulphamoylbenzoic acid methyl ester (raw product) are dissolved in glacial acetic acid and hydrogenated under normal pressure with 1 g of Pd-black. After about 30 hours, the reaction is completed. If the hydrogenation is carried out in an autoclave at 40°–50° C and 100 atmospheres gauge pressure, the reaction is completed already after 5 hours.

The solution is filtered, concentrated and the solid residue is hydrolysed with 1N-NaOH on the steam bath. The clear solution is cooled and acidified with 2N-HCl. The 4-phenoxy-3-(1-pyrrolidinyl)-5-sulphamoylbenzoic acid is recrystallised from CH$_3$OH/H$_2$O. M.p. 226°–227° C.

EXAMPLE 57

4-Phenoxy-3-(1-pyrrolidinyl)-5-sulphamoylbenzoic acid    Method I (a) 10 g of 3-amino-4-phenoxy-5-sulphamoylbenzoic acid methyl ester together with 25 g of 1,4-dibromobutane and 10 g of NaI in a mixture of acetone and DMF are heated for several days under reflux. The course of the reaction is followed by thin-layer chromatography. When the reaction is completed, the mixture is concentrated to dryness, the excess dibromobutane is extracted with ether, the mixture is decanted and the residue is saponified with 1N-NaOH. The 4-phenoxy-3-(1-pyrrolidinyl)-5-sulphamoylbenzoic acid is precipitated from the clear solution with the aid of 2N-HCl.

(b) 10 g of 3-amino-4-phenoxy-5-N,N-dimethylaminomethyleneaminosulphonyl-benzoic acid methyl ester are heated for 5 hours under reflux together with 25 g of 1,4-dibromobutane in dimethylformamide. The reaction mixture is then concentrated to dryness, the excess of dibromobutane is extracted with ether, decanted and the remaining red oil is dissolved in a small amount of methanol. The 4-phenoxy-3-(1-pyrrolidinyl)-5-N,N-dimethylaminomethyleneaminosulphonyl-benzoic acid methyl ester crystallises upon standing. It is saponified as described above with sodium hydroxide solution and the 4-phenoxy-3-(1-pyrrolidinyl)-5-sulphamoylbenzoic acid is precipitated with HCl.

EXAMPLE 58

3-(1-Pyrrolidinyl)-4-phenoxy-5-sulphamoyl-benzyl alcohol 35.2 g of brono-trifluoride etherate and, subsequently, 10 g of sodium boron hydride are added at 20° C to a solution of 38.7 g of 3-(1-pyrrolidinyl)-4-phenoxy-5-sulphamoylbenzoic acid methyl ester in 500 ml of diglyme.

The reaction mixture is stirred for 2 hours at 75° C, then cooled and at first cautiously combined with 200 ml of water. After termination of the evolution of gas, the reaction mixture was combined with 2 liters of water and the crystals that have precipitated are isolated, washed with water and dried. 24.4 g of 3-(1-pyrrolidinyl)-4-phenoxy-5-sulphamylbenzyl alcohol melting at 155° C are obtained.

EXAMPLE 59:

4-Phenylsulfoxy-3-(1-pyrrolidinyl)-5-sulphamoylbenzoic acid

A solution of 7.8 g of 4-phenylmercapto-3-(1-pyrrolidinyl)5-sulphamoylbenzoic acid in 130 ml of glacial acetic acid and 20 ml of 30% H$_2$O$_2$ is stirred at room temperature. The course of the reaction is followed by thin-layer chromatography. After 20 hours, the solution is poured into 800 ml of ice-water. The precipitate is filtered off with suction and dried. Recrystallisation from methanol/water yields 4-phenylsulphoxy-3-(1-pyrrolidinyl)-5-sulphamoylbenzoic acid in the form of yellow crystals melting at 142°–144° C, with decomposition.

EXAMPLE 60

4-Phenylsulphoxy-3-[1-(methylpyrrolidinyl)]-5-sulphamoylbenzoic acid

A solution of 6 g of 4-phenylmercapto-3-[1-(methylpyrrolidinyl)]-5-N,N-dimethylaminomethyleneaminosulphonylbenzoic acid in 70 ml of glacial acetic acid and 15 ml of 30% H$_2$O$_2$ is stirred at 5°–20° C. After 20 hours, the solution is poured into ice-water. The residue is washed with water, dried and hydrolysed for 2 hours at 100° C with 30 ml of 2N-NaOH. The hydrolysate is filtered and acidified in the cold, while stirring, with 2N-HCl to pH 2-3; thereupon, the 4-phenylsulphoxy-3-[1-(methylpyrrolidinyl)]-5-sulphamoylbenzoic acid precipitates. Recrystallisation from methanol/water yields yellow crystals melting at 143°–145° C with decomposition.

EXAMPLE 61

4-(4'-Nitrophenoxy)-3(1-pyrrolidinyl)-5-sulfamoylbenzoic acid (a)

3-N-Succinimido-4(4'-nitrophenoxy)-5-N,N-dimethylaminomethyleneaminosulfonyl-benzoic acid methyl ester.

35 g of 3-N-succinimido-4-phenoxy-5-N,N-dimethylaminomethylene-aminosulfonyl-benzoic acid methyl ester are introduced portionwise at −20° to −10° C into 200 ml of fuming nitric acid. The whole is stirred for 10 minutes and the mixture is then poured onto about 2 l of a mixture of ice and water. Stirring is continued for 1 hour, the product that has precipitated is filtered off with suction and well washed with water. The 3-N-succinimido-4(4'-nitrophenoxy)-5-N,N-dimethylaminomethyleneaminosulfonyl-benzoic acid methyl ester is obtained in a very good yield and in the form of a white crystal powder. M.p.: 260°–261° C.

(b)

4-(4'-Nitrophenoxy)-3(1-pyrrolidinyl)-5-N,N-dimethylamino-methyleneaminosulfonyl-benzoic acid methyl ester.

30 g of the imide (Example 61 a)) are suspended in about 250 ml of absolute diglyme and 22 ml of BF$_3$-etherate are added. Then, a solution of 3.2 g of NaBH$_4$ in 250 ml of absolute diglyme is added dropwise at 50° to 60° C. After 1.5 hour, the excess reducing agent is hydrolyzed with a small amount of water and the 4-(4'-nitrophenoxy)-3(1-pyrrolidinyl)-5-N,N-dimethylaminomethylene-aminosulfonyl-benzoic acid methyl ester is crystallised out with ice water. Light yellow crystals, from methanol; M.p. 216°–217° C.

(c)

4-(4'-Nitrophenoxy)-3(1-pyrrolidinyl)-5-sulfamoylbenzoic acid.

24 g of the ester (Example 61 b)) are heated for 1.5 hour in 200 ml of 1N-NaOH and a small amount of methanol as solubilizer on a steam bath until a clear solution has formed. Then, after cooling, the free acid is precipitated with 2N-HCl.

The 4-(4'-nitrophenoxy)-3(1-pyrrolidinyl)-5-sulfamoylbenzoic acid is recrystallised from a mixture of glycol-monomethyl ether and water. Light brown crystals; M.p. 235°–238° C with decomposition.

EXAMPLE 62

4-(4'-Aminophenoxy)-3(1-pyrrolidinyl)-5-sulfamoylbenzoic acid 18.5 g of 4-(4'-nitrophenoxy)-3(1-pyrrolidinyl)-5-sulfamoylbenzoic acid are dissolved in dimethylformamide and hydrogenated with Raney nickel at room temperature and normal pressure for 8 hours. After filtration, the 4-(4'-aminophenoxy)-3-(1-pyrrolidinyl)-5-sulfamoylbenzoic acid is precipitated with water. Brown crystals, from a mixture of DMF and H$_2$O; M.p. 234°–240° C with decomposition. The compound crystallises with ½ mole of dimethylformamide which cannot be eliminated even by prolonged drying under reduced pressure at 120° to 150° C.

We claim:

1. A compound of the formula

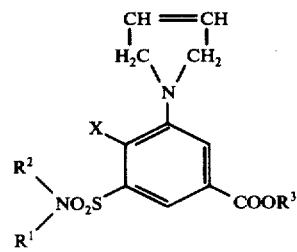

and the physiologically tolerated salts thereof, wherein R$^1$, R$^2$, and R$^3$ are hydrogen or alkyl of 1 to 4 carbon atoms; and X is phenoxy, the phenyl ring of which may be substituted by halogen, OH, NO$_2$, NH$_2$, CF$_3$, alkyl of 1 to 4 carbon atoms, alkoxy of 1 to 3 carbon atoms, or dimethylamino.

2. The compound as defined in claim 1, which is 4-phenoxy-3(3-pyrrolin-1-yl)-5-sulfamoylbenzoic acid or its methyl ester.

3. A diuretically and saluretically active composition containing 0.5 to 100 mg per dosage unit of a compound as defined in claim 1 and a pharmaceutically tolerable carrier therefor.

4. A method of treatment which comprises administering to a patient a diuretically or saluretically effective amount of a compound as defined in claim 1.

* * * * *